United States Patent [19]

Dillman

[11] 4,170,992
[45] Oct. 16, 1979

[54] FIDUCIAL POINT LOCATION

[75] Inventor: Richard F. Dillman, Lexington, Mass.

[73] Assignee: Hewlett-Packard Company, Palo Alto, Calif.

[21] Appl. No.: 867,265

[22] Filed: Jan. 5, 1978

[51] Int. Cl.$^2$ ............................. A61B 5/04
[52] U.S. Cl. .......................... 128/702; 364/417
[58] Field of Search .......... 128/206 A, 206 R; 364/417

[56] References Cited

U.S. PATENT DOCUMENTS

| | | | |
|---|---|---|---|
| 3,267,933 | 8/1966 | Mills et al. | 128/2.06 A |
| 3,267,934 | 8/1966 | Thornton | 128/2.06 A |
| 3,598,110 | 8/1971 | Edmark | 128/2.06 A |
| 3,616,791 | 11/1971 | Harris | 128/2.06 A |
| 3,940,692 | 2/1976 | Neilson | 128/2.06 A |
| 4,023,564 | 5/1977 | Valiquette et al. | 128/2.06 A |

FOREIGN PATENT DOCUMENTS 1962077 6/1971 Fed. Rep. of Germany ..... 128/2.06 A

OTHER PUBLICATIONS

Holsinger et al., "IEEE Transactions on Biomedical Engineering", vol. 18, No. 3, May 1971, pp. 212–217.

*Primary Examiner*—William E. Kamm
*Attorney, Agent, or Firm*—Donald N. Timbie

[57] ABSTRACT

Ventricular ectopic heartbeats are detected by comparing the ECG wave for a current heartbeat with the ECG wave of a heartbeat considered to be normal for that patient. The waves are aligned with their fiducial points in time coincidence, and the fiducial points are located at the centroids of the ECG waves.

5 Claims, 13 Drawing Figures

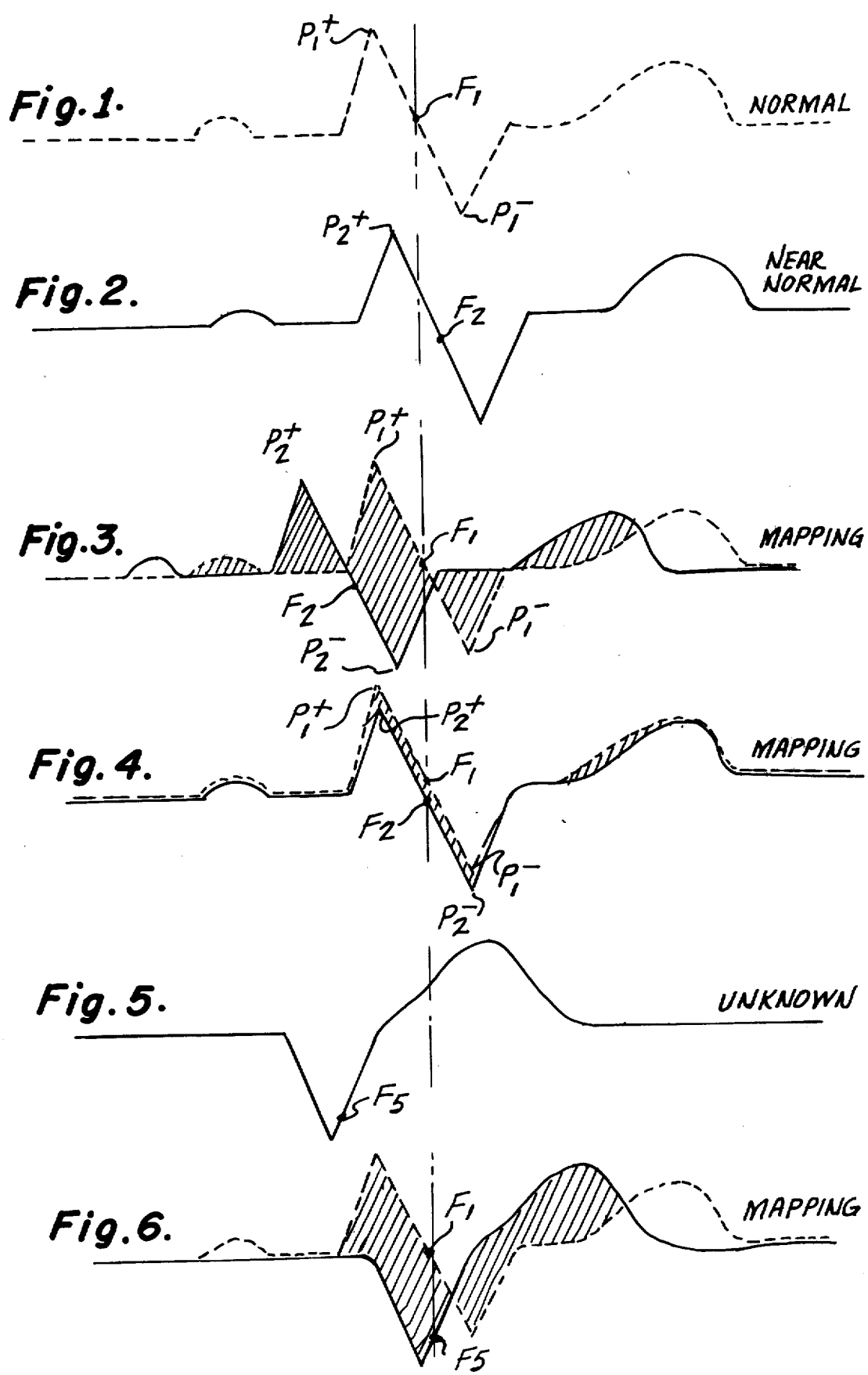

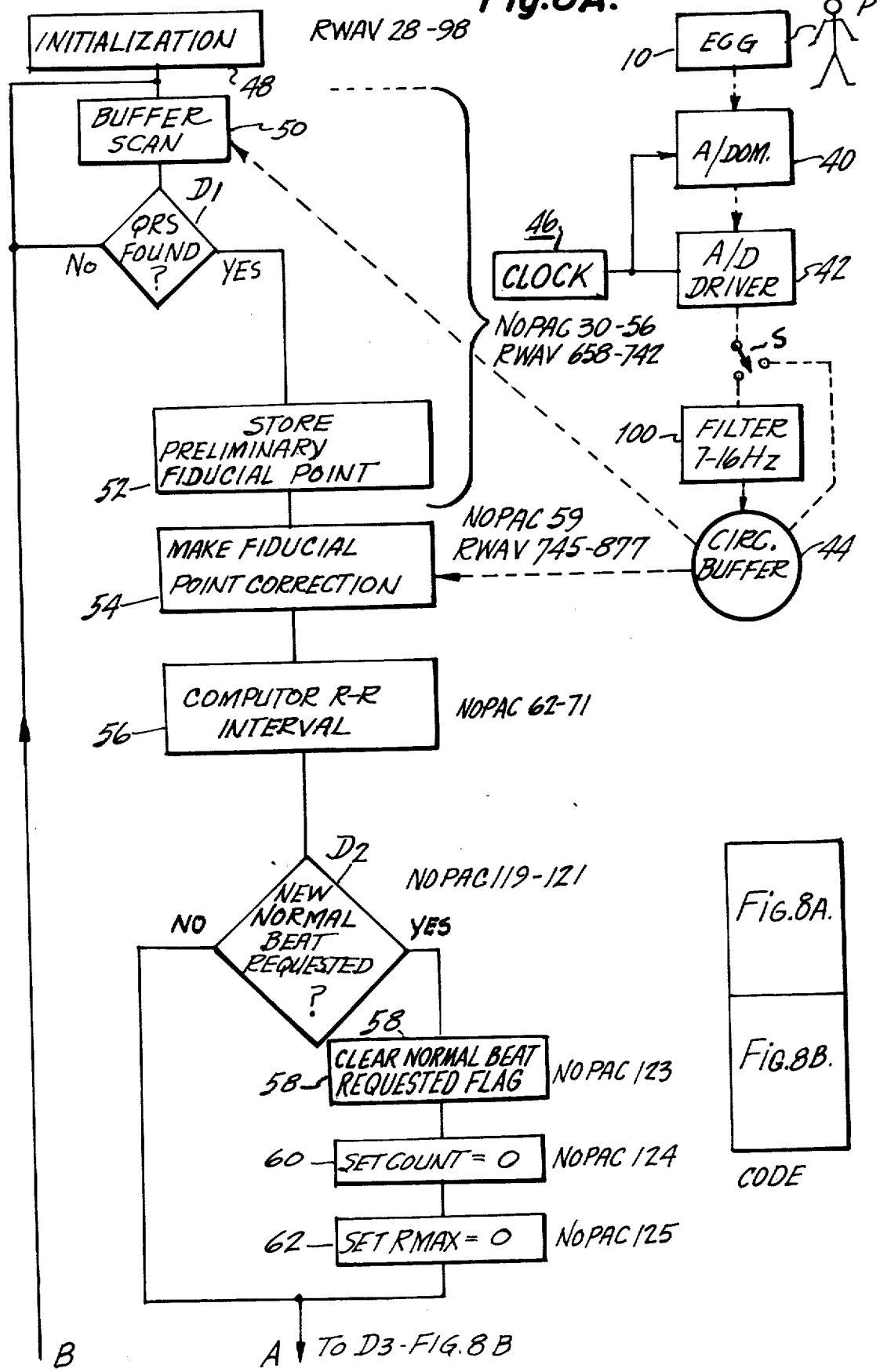

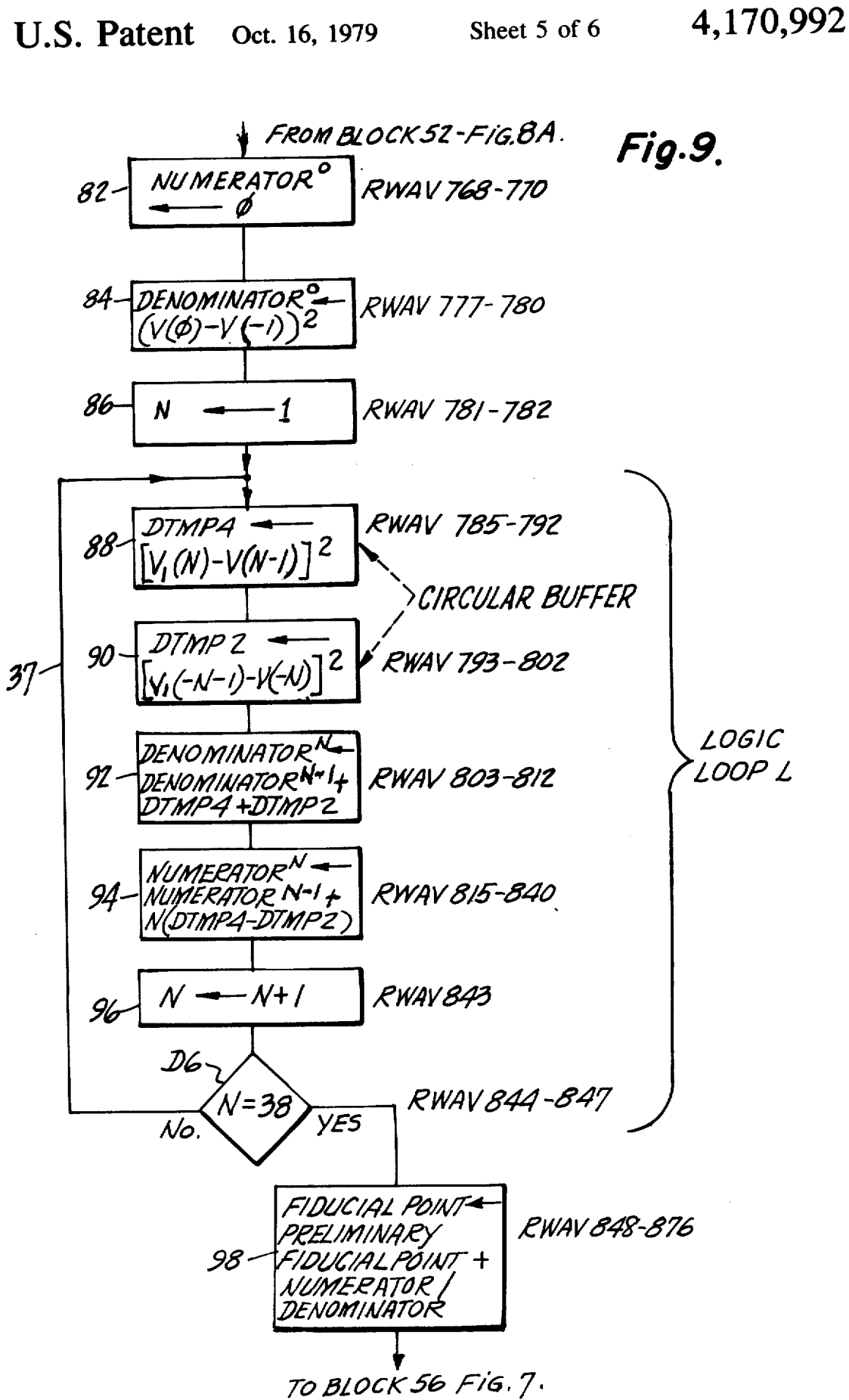

FIDUCIAL POINT LOCATION

BACKGROUND OF THE INVENTION

The presence of ventricular ectopic beats in the heart action of a patient often gives early warning of impending conditions that can be fatal. It is important, therefore, that equipment used to monitor the patient's condition provide indicia of their presence so that timely remedial action can be taken. However, it is equally important that the frequency of false indicia be reduced to a minumum in order that the time of medical attendants may be used efficiently and to prevent the presence of the indicia from being ignored. Unfortunately, however, present monitors leave much to be desired in this regard.

One method of identifying a ventricular ectopic heartbeat is by comparing its ECG wave with a wave that is considered to be normal for the particular patient involved. Any one of the number of empirical formulae can be used for this purpose, but in addition to certain physiological data, many require an input as to the measure of correlation between the form of the ECG wave for the heartbeat being examined and the form of the ECG wave representing the normal heartbeat. A reliable measurement can be attained only if the waves are effectively aligned, so that the portions of each that correspond to the same part of the heartbeat cycle are in time coincidence. This result can be attained by locating a single point in each heartbeat cycle, known as a fiducial point, that uniquely occurs at the same functional point in any ECG wave and aligning the waves with their points in time coincidence. If the location of the fiducial points is not accurate, the degree of form correlation, even for identical waves, can be far less than the actual 100 percent. In the present state of the art, the location of the fiducial points is unreliable, so that too many ectopic beats are not detected or too many false alarms are given.

In determining whether a particular heartbeat is a ventricular ectopic beat, data relating to the time between it and the previous beat, the average time between beats, and the average deviation of the beats from the average time between them is often used. If, as in the prior art, the fiducial point is not properly located, this data will be inaccurate so as to make the identification of a ventricular ectopic beat unreliable.

In making form correlation, data as to the area of non-overlap between the ECG wave being examined and the ECG wave that is considered normal is often used. In prior methods, correlation has depended on the sum of the absolute differences in the areas of corresponding samples of the wave being examined and the normal wave, so that the correlation changes with amplitude. This makes it difficult to identify the ectopic beat.

BRIEF DISCUSSION OF THE INVENTION

In accordance with this invention, the fiducial point is located in such manner that the portions of the cycle of the greatest clinical interest, namely, those that occur when the ventricle is stimulated, have a greater effect on the location of the fiducial point than other portions of the heartbeat cycle. This can be accomplished by locating the fiducial point at the centroid of the ECG wave in accordance with the following expression in which the times $t_1$ and $t_2$ respectively occur before and after the QRS wave, T is the time after $t_1$ at which the centroid occurs, M is the order of the derivative, and n is the power to which it is raised.

$$T = \frac{\int_{t_1}^{t_2} t \left( \frac{d^M V}{dt^M} \right)^n}{\int_{t_1}^{t_2} \left( \frac{d^M V}{dt^M} \right)^n} \tag{1}$$

If n is an odd integer, the absolute value of dV/dt must be used in the above equation, so that negative derivatives contribute in the same way as positive derivatives. It is possible to use $M = \phi$. The program for making the calculation of T is unimportant and, as will be explained in detail, the first derivative for at least the lower frequencies can be derived by a filter coupled between the ECG machine and the means making the computation.

THE DRAWINGS

FIG. 1 shows a normal cardiac waveform;

FIG. 2 shows a nearly normal cardiac waveform to be analyzed for a ventricular ectopic beat;

FIG. 3 illustrates the alignment of the cardiac waveforms of FIGS. 1 and 2 by superimposition of fiducial points that are respectively located at the peaks having the greatest amplitude;

FIG. 4 illustrates the alignment of the cardiac waveforms of FIGS. 1 and 2 by superimposing fiducial points that are located at the centroid in accordance with the present invention;

FIG. 5 shows a cardiac waveform differing substantially from the normal cardiac waveform of FIG. 1;

FIG. 6 shows the alignment of the cardiac waveform of FIG. 5 with the normal cardiac waveform of FIG. 1 utilizing the fiducial points located in accordance with this invention;

Figure 9A:
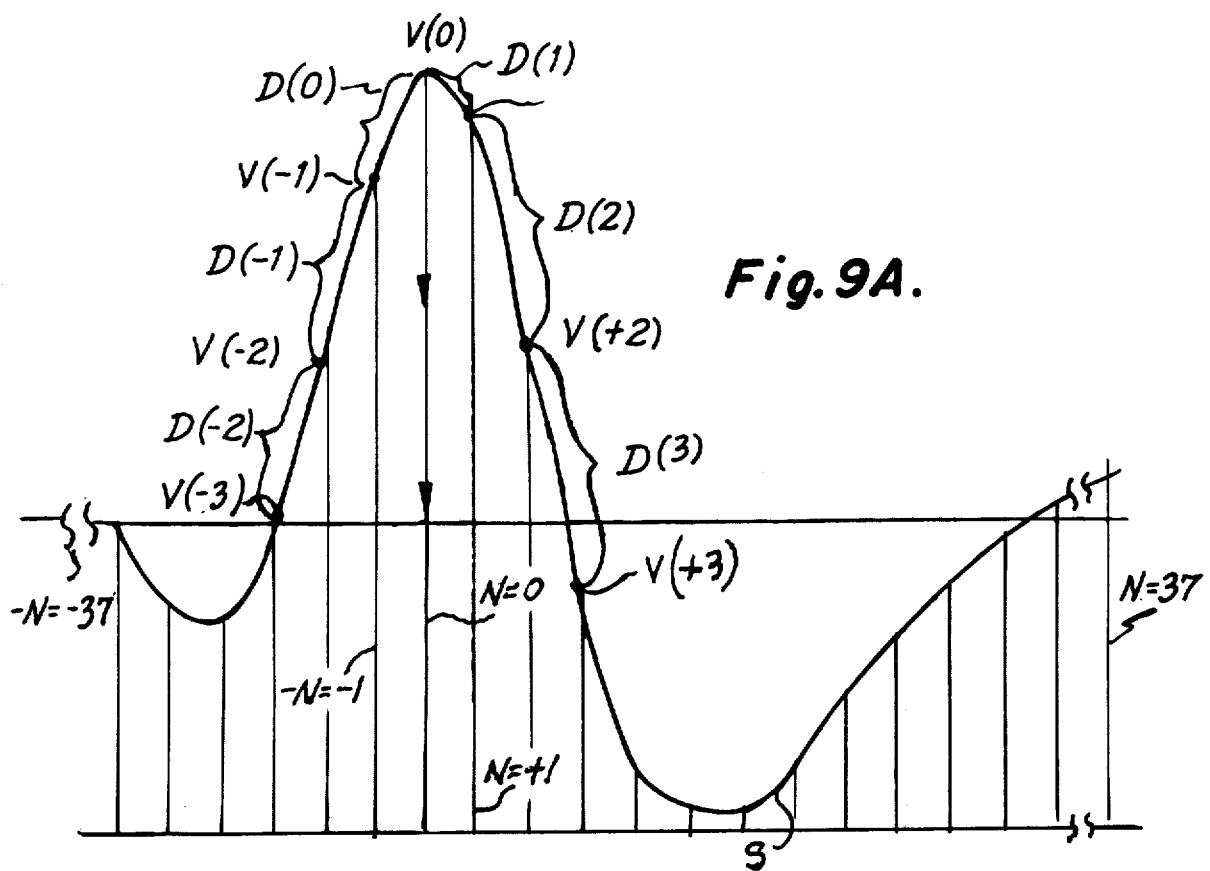
Figure 9B:
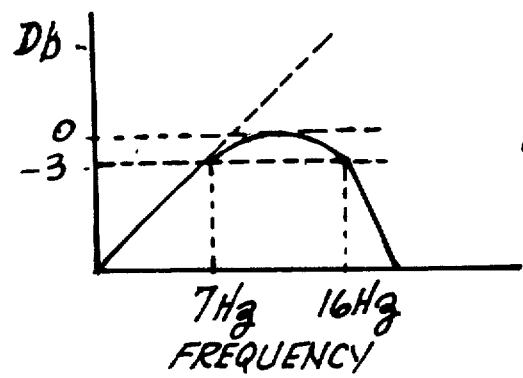
Figure 8B:
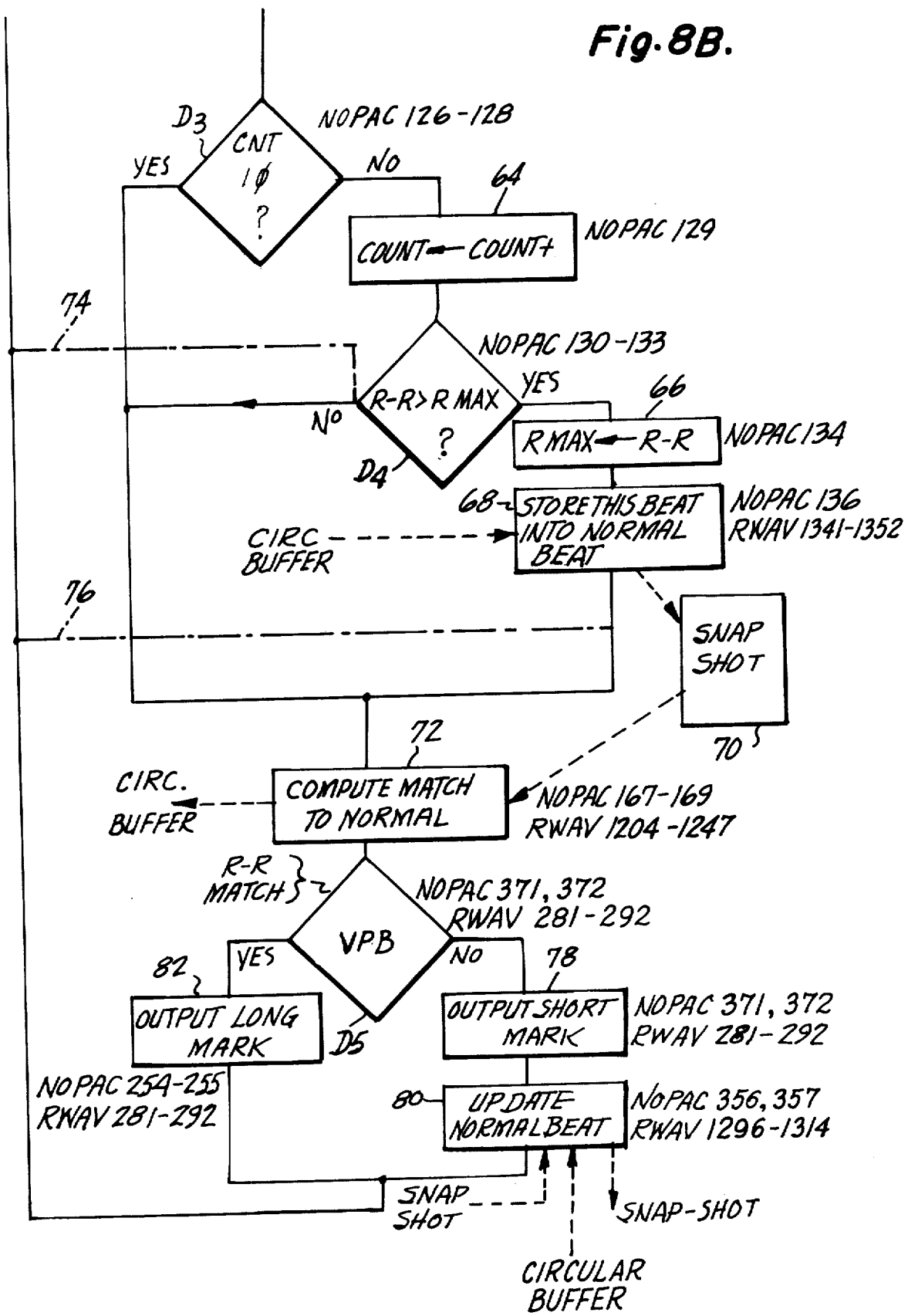

FIGS. 8A and 8B together are a flow chart for one computer program that can be used with monitoring systems that provide indicia of the presence of ectopic beats in the ECG waves derived from a patient;

FIG. 9 is a flow chart of one computer program that may be used to determine the location of the fiducial point in accordance with this invention;

FIG. 9A is a QRS waveform used in explaining the operation of FIG. 9;

FIG. 9B is a graph of a filter characteristic shown in FIG. 8A; and

Figure 10:
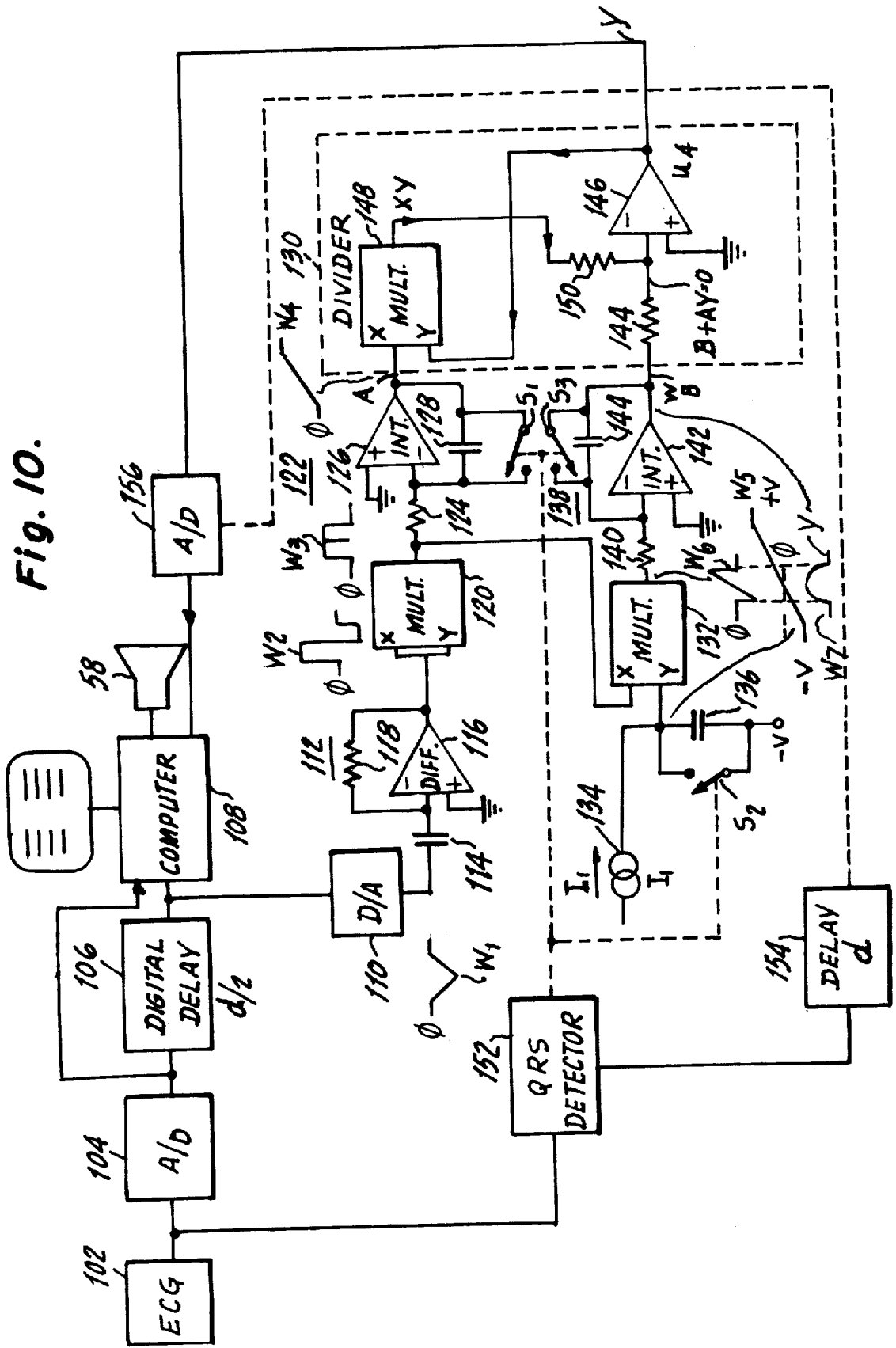

FIG. 10 illustrates a circuit for locating the fiducial point in accordance with this invention.

FIGS. 1 through 6 illustrate the situation where the degree of correlation between the forms of two ECG waves is determined by the amount of non-overlap between them. It will be understood that actual graphs of the waves need not be used, and that the area of non-overlap can be determined by finding the difference between cotemperal samples of the waves occurring between times of interest when the fiducial points coincide in time.

Mapping of Waves

FIG. 1 shows an ECG wave in a dotted line that is considered to be normal for a given patient, and FIG. 2 shows a wave that would also be considered normal because it is nearly identical to the wave of FIG. 1. The only difference is that the amplitude of the most positive peaks $P_1+$ of the wave of FIG. 1 is slightly greater than the amplitude of its most negative peak $P_1-$, whereas in FIG. 2, the amplitude of the most negative peak $P_2-$ is slightly greater than the amplitude of its most positive peak $P_2+$.

If the dotted line ECG wave of FIG. 1 and the solid line ECG wave of FIG. 2 are mapped by locating the fiducial points at the peaks of greatest amplitude, the peaks $P_1+$ and $P_2-$ will be aligned in time, as indicated in FIG. 3. The area of non-overlap shown by the shaded area of FIG. 3 is so large that the wave of FIG. 2 would be considered ectopic. Such a slight difference in peak amplitudes and the resulting false indication of an ectopic beat can be caused by the movement of the patient or of the electrodes, or by the patient's breathing.

If, however, the fiducial points $F_1$ and $F_2$ of the waves of FIGS. 1 and 2 are each located at a centroid in accordance with this invention, the area of non-overlap is very small, as shown in FIG. 4, so that the solid line ECG wave of FIG. 2 would be indicated as being normal.

Now consider the solid line ECG wave of FIG. 5 that differs substantially in shape from the normal dotted line ECG wave of FIG. 1. The fiducial point $F_5$ of the wave of FIG. 5 is located at a centroid, in accordance with this invention. When the waves are mapped, the results are as shown in FIG. 6. The area of non-overlap shown by the shading is so large that the ECG wave of FIG. 5 would be indicated as representing an ectopic beat.

Overall System

Figure 7:
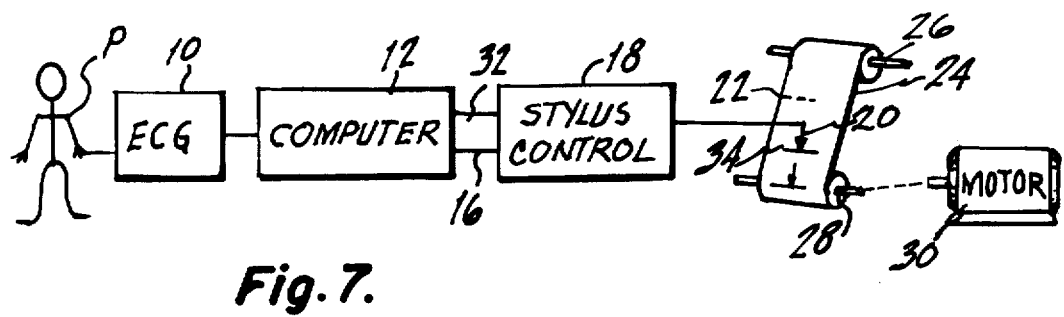
FIG. 7 is a block diagram of the portions of a monitoring system in which indicia is provided whenever an ECG signal represents an ectopic beat.

FIG. 7 is a block diagram of the kind of known monitoring systems in which the present invention can be used to advantage. An ECG machine 10 supplies ECG signals indicative of the heartbeat of a patient P to a computer 12. When the beat is not ectopic, the computer 12 provides a signal via a lead 16 to a stylus control means 18 so as to cause the stylus 20 to make a short mark 22 on a tape 24 that is transverse to the direction in which the tape 24 is moved by rollers 26 and 28 and a motor 30. When, however, the beat is ectopic, the computer 12 provides a signal via a lead 32 to the stylus control means 18 so as to cause the stylus 20 to make a long mark 34 on the tape 24.

Flow Chart for Overall System

The detailed operation of a monitoring system, such as shown in FIG. 7, is now explained by reference to FIGS. 8A and 8B. They include a portion of a flow chart applicable to any computer for a program set forth at the end of the specification that may be used to control the computer 12 of FIG. 7 if it is an HP Computer Model 2109 or 2113. The steps of the program that apply to various parts of the flow chart are written adjacent the appropriate blocks. Information flow is indicated by dotted lines and logic flow by solid lines.

Signals representing heart action are derived from the patient P by the ECG machine 10, as in FIG. 7, and applied to an A/D converter 40. Its output is coupled via an A/D driver 42 and a switch S to a circular buffer 44. The converter 40 and driver 42 are both synchronized by a digital clock 46. Part of the initialization of the system is achieved by carrying out program steps RWAV 28-98 indicated by the block 48 to purge the system of all information signals. One storage position of the circular buffer 44 is then examined by a buffer scan 50. If no QRS wave is present, a decision is made, as indicated by the decision block $D_1$, to cause the buffer scan 50 to examine the next storage position in the circular buffer 44. The process continues until a QRS wave is detected. The time after initialization at which the first QRS wave occurs is stored in a preliminary fiducial point storage, as indicated by block 52. These functions are controlled by program steps NOPAC 30-56 and RWAV 658-742, so that the buffer scan block 50 in combination with the decision block $D_1$ constitutes a QRS detector of a known type that sets the time of the preliminary fiducial point at the time of the positive or negative peak having the greatest amplitude in each QRS wave, as illustrated in FIGS. 1 or 2.

After the preliminary fiducial point is stored by the block 52, the ECG wave then in the circular buffer 44 is examined, as indicated in the block 54, to determine the time of the corrected fiducial point with respect to the time of the preliminary fiducial point. This has been done in a number of ways, but if it is to be determined in accordance with the principles of this invention, as indicated by expression (1), it may be accomplished by carrying out the program steps NOPAC 59 and RWAV 745-877 in a manner to be described in detail in connection with FIG. 9.

Identification of "Normal" Cycle

After initialization, it is essential to identify and store information as to the heartbeat cycle that is to be considered "normal". One heartbeat cycle that can be used for this purpose is the one occurring immediately after the longest interval between any of about ten successive cycles. Block 56 measures the intervals, known as R to R intervals, between successive corrected fiducial points determined by the block 54 in accordance with program steps NOPAC 62-71. Upon operator request, the normal beat request flag is set by means not shown to inform the decision block $D_2$ that a new normal heartbeat cycle is requested. This causes the block 58 to clear the flag and the block 60 to set the count, to be explained, to zero under control of program step NOPAC 124. The block 62 then sets the maximum interval between heartbeat cycles $R_{MAX}$, to be explained, to zero under the control of step NOPAC 124. The count referred to is the count in blocks 60 and 64. With this set to zero, the count in block 64 becomes unity under the control of step NOPAC 129, so that the output of the decision block $D_3$, that determines if the count has reached ten under the control of steps NOPAC 126-128, is NO. The decision block $D_4$ determines under the control of steps NOPAC 130-133 whether the R to R interval is greater than $R_{MAX}$. $R_{MAX}$ is initially made equal to zero by block 62, so that the output of $D_4$ is YES. This, in turn, causes a block 66 to substitute the first R to R interval for $R_{MAX}$ in accordance with step NOPAC 134. Block 68 stores this heartbeay cycle from the circular buffer 44, as well as information as to the location of its corrected fiducial point, in a snapshot memory 70 under the control of steps NOPAC 136 and RWAV 1341-1352.

If the R to R intervals between the next nine successive heartbeat cycles are less than the first one, the output of the decision block $D_4$ is negative and the match block 72 successively superimposes each of these cycles from the circular buffer 44 on the normal beat from the snapshot memory 70, which, in this case, was the first cycle, with their corrected fiducial points occurring at the same time. Successive cycles are compared until one of them follows a larger R to R interval, in which event it is stored in the snapshot memory 70. This process continues until the count equals ten or some other arbitrarily selected value, at which point the output of the decision block $D_3$ is YES. From this point on, unless a new normal beat is requested by activating the normal beat request flag, each successive cycle of of a beat from the circular buffer 44 is matched by the block 72 with the normal cycle stored in the snapshot memory 70 and the correlation (as explained below) is calculated.

In order to prevent the match block 72 from comparing each of the first ten heartbeat cycles with the cycle stored in the snapshot memory 70, the NO output of the decision block $D_4$ and the output of the store block 68 can be applied so as to activate the buffer scan 50, as indicated by the dash-dot lines 74 and 76. Thus, the match block 72 is not activated until the output of the decision block $D_3$ is YES, which occurs ten cycles after a new normal beat is requested.

Correlation

There are several formulae which can be used to compare beats after they are aligned. As a class, they are called correlation. Several investigators have employed a "cross correlation coefficient":

$$\frac{\Sigma V_1(N) \cdot V_2(N)}{\left[\left(\Sigma[V_1(N)]^2\right) \cdot \left(\Sigma[V_2(N)]^2\right)\right]^{\frac{1}{2}}} \quad (2)$$

This formula has rather formidable computational difficulties due to the large number of multiplying operations involved. It yields a number which varies from 0 for a worst case mismatch to 1 if $V_1$ and $V_2$ differ only in amplitude.

An attempt to get around the computational difficulties is the absolute area of non-overlap calculation:

$$\Sigma |V_1(N) - V_2(N)| \quad (3)$$

This formula is certainly simpler but, unlike cross correlation, it is not dimensionless. That is, if $V_1$ and $V_2$ change proportionally, the correlation changes.

This problem is removed in the system described by normalization:

$$A = \frac{\Sigma |V_1(N) - V_2(N)|}{\Sigma [|V_1(N)| + |V_2(N)|]} \times 512 \quad (4)$$

The formula is now dimensionless and equal to 512 for a worst case mismatch and to 0 for perfect identity. In the system described, the above formula is multiplied by 512 so that integer arithmetic can be used. This latter computation is done in match block 72 in accordance with the steps NOPAC 167-169 and RWAV 1204-1247.

Having correlated the current and normal waves by determining the normalized area of non-overlap A in the matching block 72, there are a number of acceptable ways of determining whether a beat is a ventricular ectopic beat. They generally require inputs as to the time R between the beat being examined and the previous beat, the average time Z between beats, and the average deviation W of the beats from the average time Z between them. A particularly advantageous way of making the determination from these inputs is to substitute them into the following expression:

$$B = \frac{R - Z}{\frac{Z}{8} + W} \times 100 + 250 \quad (5)$$

This is done in decision block $D_5$ under control of program steps NOPAC 177-319. . It can be seen, for example, that, if the beat being examined follows the previous beat by a time R equal to average time Z between beats, then B=250, and that if R is less than Z, B is reduced. If B is less than 125, it is arbitrarily assigned a value of 125. If A, the normalized area of non-overlap, is greater than B, the beat is considered to be ectopic and the output of the decision block $D_5$ is YES. When this occurs, a block 82 outputs a long mark on the tape or other record media under the control of program steps NOPAC 254 and 255 and RWAV 281-292.

If the decision block $D_5$ concludes that the current beat is not ectopic, so that the output of the block $D_5$ is NO, a block 78 outputs a short mark on a tape or other record media under the control of program steps NOPAC 371 and 372 and RWAV 281-292. Block 80 updates the normal cycle in the snapshot memory 70 by adding $\frac{1}{8}$ of the difference between the normal cycle and the current cycle to the normal cycle, as indicated by $$V_s(N) \leftarrow V_s(N) + \frac{1}{8}[V(N) - V_s(N)] \quad (6)$$

under the control of program steps NOPAC 356 and 357 and RWAV 1296-1314. This makes the normal heartbeat cycle stored in the snapshot memory 70 a running average. After block 82 has produced a long mark or after block 80 has updated the snapshot memory 70, the scan buffer 50 is advanced to the next cycle stored in the circular buffer 44, and the process is repeated.

Location of the Fiducial Point

There are a number of means that can be used in the block 54 of FIG. 8A for determining the location of the fiducial points in accordance with equation (1) so that they are located at the centroid in accordance with this invention. The required integration is performed between an earlier limit occurring prior to the heartbeat cycle and a later limit occurring after it. The process of integration can start at the lower limit and proceed to the higher limit, or it can start at an intermediate point in the cycle and proceed forward to the later limit and backward to the earlier limit at the same time. One way of carrying out the latter method is illustrated by the flow chart of FIG. 9 in which the steps of the program at the end of the specification are indicated near the appropriate blocks. Assume that the QRS portion of a wave representing a heartbeat cycle is as shown by the curve of FIG. 9A and that the samples provided by the A/D converter 40 of FIG. 8A are at times indicated by the vertical lines. The samples are farther apart than normal in order to clarify the drawing and will occur during the portions of the heartbeat cycle other than the QRS portion shown. For this particular wave, the preliminary fiducial point determined by the QRS detector comprised of the blocks 50 and $D_1$ of FIG. 8A will be at the sample indicated by V(O) because it has the greatest amplitude from the baseline b which is at ground potential.

The blocks of the flow chart of FIG. 9 that are now to be described set up initial conditions for the logic loop L that performs the integration necessary to determine the respective values of the numerator and denominator of equation (1) for each heartbeat cycle. The purpose of these initial conditions will be apparent when the operation of the loop L is considered.

Block 82 sets the initial value of numerator$^O$ to zero in accordance with program steps RWAV 768-770. Following this, the block 84 sets the initial value of the denominator$^O$ equal to the square of the difference between the amplitude of the sample V(O) and the amplitude of the sample V(-1) in accordance with steps RWAV 777-780. The letter D and the numbers in the parenthesis following it in FIG. 9A designate the difference between successive amplitude samples. These differences are the samples of slope to be used in making calculations of the location of the fiducial point in accordance with the equation (1). If there are to be 75 slope samples including the zero$^{th}$ sample, N varies from 1 to 37. The block 86 sets the initial value of N at one in accordance with steps RWAV 781 and 782.

Turning now to the loop L, block 88 operates in response to steps RWAV 785-792 to compute $$[V(N) - V(N-1)]^2 \tag{7}$$

for successive values of N from the lowest value of N permitted by the block 86, which is one, until a value of N equal to 38, if there are to be 75 samples in the integration. The output of the block 88 for each value of N is stored in a temporary memory DTMP 4. Block 90 then operates in response to steps RWAV 793-802 to compute $$[V(-N-1) - V(-N)]^2 \tag{8}$$

for successive value of N from 1 to 37. The output of the block 90 for each value of N is stored in DTMP 2. A block 92 then calculates the value of the new denominator$^N$ in accordance with steps RWAV 803-812. The new denominator$^N$ is equal to the value of the previous or initial denominator plus the information stored in DTMP 4 plus the information stored in DTMP 2. A block 94 then calculates in accordance with steps RWAV 815-840 the value of the new numerator$^N$, which is equal to the old numerator plus N times the information in DTMP 4 minus N times the information in DTMP 2. At this time, a block 96 substitutes N+1 for N in response to step RWAV 843. If N is less than 38, a decision block D$_6$ has a negative output that causes a repetition of the calculation just described at a value of N that is one unit larger. The calculations indicated by the above blocks 88, 90, 92, 94 and 96 are repeated for successive values of N from 1 to 37. When, however, N=38, the output of the decision block D$_6$ is YES and causes a block 98 to compute in accordance with steps RWAV 848-876 the time of occurrence of the corrected fiducial point. This is done by adding to the preliminary fiducial point indicated by the QRS detector a fraction with the same units as N in which the numerator is the numerator provided by the block 94 and the denominator is the denominator provided by the block 92. This information is then supplied to the block 56 of FIG. 8A.

Summary of Operation of FIG. 9

The expressions for the numerator provided by the block 94 is $$\text{numerator}^N \leftarrow \text{numerator}^{N-1} + N[(V[N] - V[N-1])^2 - (V[-N-1] - V[-N])^2] \tag{9}$$

and the expression for denominator$^N$ provided by the block 92 is $$\text{denominator}^N \leftarrow \text{denominator}^{N-1} + [V(N) - V(N-1)]^2 + [V(-N-1) - V(-N)]^2. \tag{10}$$

At the time of initialization, numerator$^O$ is made equal to zero by the block 82, and denominator$^O$ is made equal to $[V(O)-V(-1)]^2$ by the block 84. Then N is made equal to 1 by the block 86, so that after block 94 on the first pass $$\text{numerator}^1 = 0 + 1[(V[1] - V[0])^2 - (V[-2] - V[-1])^2 \tag{11}$$

and $$\text{denominator}^1 + [V(0) - V(-1)]^2 + [V(1) - V(0)]^2 + [V(-2) - V(-1)]^2. \tag{12}$$

Modification of FIGS. 8 and 9

Fourier analysis of a heartbeat cycle, such as that shown in FIG. 9A, shows that the frequencies involved generally fall between 0.5 and 50 Hz, and that most of the energy lies below 16 Hz. Whereas there is some noise at these lower frequencies in the signals provided by the ECG machine 10 of FIG. 8A, there is also a great deal of noise at the higher frequencies. The high frequency noise can be attenuated by insertion of a filter between the output of the ECG machine 10 and the input of the circular buffer 44 without interfering too much with the information contained in the signal. An analog filter could be inserted between the ECG machine 10 and the A/D converter 40 or, as in FIG. 8A, a digital filter 100 can be connected between the A/D driver 42 and the circular buffer 44 by placing the switch S in the proper position. Of course, differentiation is filtering, but preferably the filter 100 may have a bandpass characteristic passing through the origin of response vs. frequency and having half-power points located at 7 Hz and 16 Hz, as shown in FIG. 9B. This would reduce the effect of noise. Inasmuch as the lower frequencies are effectively differentiated by the filter 100, there is no need of differentiating a second time, as is done in FIG. 9 unless, of course, the second derivative is to be used at low frequencies, i.e., M is to equal 2 in equation (1). Accordingly, if the filter 100 is used and the first derivative at low frequencies is desired, the computer program would have to be changed in ways known to those skilled in the art so as to eliminate the term $-V(N-1)$ from the calculation performed by the block 88 and to eliminate the term $-V(-N)$ from the calculation performed by the block 90. The RWAV and NOPAC programs include both filtering and differentiation. Either could be eliminated but it would be preferable to retain the filtering because of noise consideration. It should be noted, however, that the amplitude V in the remaining terms is different than before because of the presence of the filter 100.

FIG. 10 shows a circuit for calculating the location of the fiducial point of a cardiac waveform so that it will be located at the centroid in accordance with this invention. The ECG signals which represent normal beats, as well as ventricular ectopic beats, are supplied by a source 102 to an A/D converter 104. Its output is applied to a point in a computer 108 corresponding to the input of the A/D driver 42 of FIG. 8A. The output of the converter 104 is also applied to a delay means 106 that delays the signals by an amount d/2 that is equal to half the duration d of the longest QRS wave to be expected, e.g., d=300 ms. The output of the delay means 106 is applied to a converter 110 that restores it to the same shape it had at the output of the ECG source 102. The output of the D/A converter 110 is coupled to a differentiator 112 comprised of a capacitor 114 coupled between the output of the D/A converter 110 and the inverting input of an operational amplifier 116, a resistor 118 connected between the output of the amplifier and its inverting input, and a ground connection for the non-inverting input.

The output of the differentiator 112, (dV/dt), is applied to X and Y inputs of a multiplier 120 so as to produce a signal $(dV/dt)^2$ at its output. The output of the multiplier 120 is coupled to an integrator 122 which is comprised of a resistor 124 connected between the output of the multiplier 120 and the inverting input of an operational amplifier 126, a capacitor 128 connected between the output of the amplifier 126 and its inverting input, a normally closed switch $S_1$ shunting the capacitor 128, and a ground connection for the non-inverting input of the amplifier 126. As will be explained, the output of the amplifier 126, which is $$\int_{t_1}^{t_2} \left(\frac{dV}{dt}\right)^2$$

is connected to an input A of a divider contained within the dotted rectangle 130.

The signal $(dV/dt)^2$ at the output of the multiplier 120 is also applied to the X input of a multiplier 132. Its Y input is connected to the junction of a source 132 of constant current $I_1$ and one side of a capacitor 136. The other side of the capacitor 136 is connected to a point of negative potential $-V$, and a normally closed switch $S_2$ is connected in shunt with the capacitor 136. The capacitance of the capacitor 136 is $I,d/2V$. The voltage applied to the Y input of the multiplier 132 is proportional to the time after the switch $S_2$ is opened, so that the output of the multiplier 132 is $t(dV/dt)^2$.

The output of the multiplier 132 is applied to an integrator 138 comprised of a resistor 140 connected between the output of a multiplier 132 and the inverting input of an operational amplifier 142, a capacitor 144 shunted by a normally closed switch $S_3$ and connected between the output of the amplifier 142 and its inverting input, and a ground connection for the non-inverting input of the amplifier 142. As will be explained, the output of the amplifier 142 is $$\int_{t_1}^{t_2} t\left(\frac{dV}{dt}\right)^2$$

This signal is applied to the input, B, of the divider 130.

The particular construction of the divider 130 is unimportant, but in this particular illustration, it is comprised of a resistor 144 connected between the B input of the divider 130 and the inverting input of an operational amplifier 146 having its non-inverting input connected to ground. Also included is a multiplier 148 having its X input connected to the input A of the divider 130 and its Y input connected to the output of the amplifier 146. A resistor 150, having the same value as the resistor 144, is connected between the output of the multiplier 148 and the inverting input of the operational amplifier 146. The signal at the output of the divider 130 is $$\frac{B}{A} \text{ or } \frac{\int_{t_1}^{t_2} t\left(\frac{dV}{dt}\right)^2}{\int_{t_1}^{t_2} \left(\frac{dV}{dt}\right)^2}$$

The output of the ECG amplifier 102 is also applied to the input of a QRS detector 152 that provides a pulse at some point within the QRS portion of the cardiac waveform. The timing of this pulse cannot be used as the time of a fiducial point because it does not always occur at the same functional point in the cardiac waveform. The pulse at the output of the QRS detector 152 is applied to means (not shown) for opening the switches $S_1$, $S_2$ and $S_3$ and also to a delay means 154 having a delay of d ms. The delayed pulse at the output of the delay means 154 is applied to means (not shown) to cause an A/D converted 156 to sample the output of the divider 130 and input this information to a point in the computer 108 corresponding to the input to the block 56 of FIG. 8A.

The purpose of introducing the various delays into the circuit is to establish the limits of integration, i.e., $t_1$ and $t_2$ of the expression (1). When the switches $S_1$, $S_2$ and $S_3$ are closed, as they normally are, the circuits are inoperative. At the approximate center of the QRS wave, the QRS detector 152 outputs a pulse that opens the switches $S_1$, $S_2$ and $S_3$ and starts the calculation at time $t_1$. Assuming that the QRS wave will not have a duration greater than d, the fact that the wave at the output of the D/A converter 110 is delayed by d/2 means that the switches open so as to permit calculations to start at some point before the QRS wave begins. The pulse outputted by the QRS detector 152 is delayed by a time d in the delay means 154 before it activates an A/D converter 156 at a time $t_2$. Thus, the computer 108 has both the ECG waveform and information as to location of the fiducial point and can compute the area of non-overlap or any other correlation calculation or integrative measure of difference between this ECG waveform and any other previous input in a like manner, including a beat designated as normal. When the difference exceeds a predetermined amount, an indication is made to the effect that the heartbeat cycle is ectopic, but if the difference is less than the said predetermined amount, an indication is made to the effect that the heartbeat cycle is not ectopic.

By way of illustration, if the ECG waveform at the output of the D/A converter 110 is as indicated at $W_1$, the outputs of the differentiator 116, the multiplier 120, and the integrator 122 will be as represented by the waveforms $W_2$, $W_3$ and $W_4$, respectively. The voltage across the capacitor 136 will vary linearly from a value of $-V$ at some time prior to the departure of $W_1$ from zero to a value of $+V$ at some time after $W_1$ returns to zero, as indicated by the waveform $W_5$. $W_5$ and $W_3$ are applied to the inputs of the multiplier 140 so as to produce an output as indicated by the waveform $W_6$. Integration of this output by the integrator 138 produces a parabolic output indicated by the waveform $W_7$. The division of $W_7$, at the B input of the divider 130, by $W_4$, at the A input, yields a value Y, after all calculations have been completed, that represents the difference in time between the preliminary fiducial point determined by the QRS detector 152 and the final fiducial point determined in accordance with this invention. In this particular example, the preliminary fiducial point and the final fiducial point occur at the same time, i.e., at the apex of $W_1$, so that Y at this point is zero; as indicated by the fact that the parabola $W_7$ returns to zero. Although not shown, means are provided for closing the switches $S_1$, $S_2$ and $S_3$ in between the waves so as to discharge the capacitors 128, 136 and 144, and set the initial conditions for determining the fiducial point of the next ECG wave.

Whether the timing of the fiducial point of an ECG waveform is made to be in accordance with equation (1) by a computer or by a circuit, it occurs at the proper point so that the R to R intervals are correct. The measure of these intervals appears at the output of the block 56 of FIG. 8A and is used in identifying an ectopic beat, but it can be used by other means for other purposes where its accuracy is also important.

```
                                        REVISED    24 AUG 77
                                   NAM NUPAC REVISED   24 AUG 77

PVC FINDER FOR NON-PACED PATIENTS. REVISED 24 AUG 77.

ENT NUPAC
                          EXT HTLHL,LHTLB,RTCNT,RTOUT
                          EXT AGE,ALSUB,BCNT,BPATH,BTRMN,BTOBT,BTOD,BUFL,DELAY
                          EXT CSLEN,DSNAP,DTORD,ERASE,ERFLG,FINDX,FPINX,FPTSB
                          EXT GOSFL,INDX,LINE1,LINE2,MATCH,MHITE,MRDEV
                          EXT MRTCR,MSLN1,MSLN2,MSNAP,MSNSN,MSPT1,MSPT2,MSPT3
                          EXT N2,NAGE,NBTM1,NOTSB,NOISE,NSNAP,OLMHT
                          EXT OUTPT,OUVPR,PATH,PEAK,POP,RTOK,RWVSB
                          EXT SCAN,SECTR,SNPAD,SORT,TEMP1,TEMP2,FHLY
                          EXT USNAP,VCNT,VFIB,VFINX,VRCNT,VRPT,WIOSB,WIDTH
                          MIC EHS,1H5601B,4
                          MIC HRT,1H5600B,4
             ( IC COM,1H5523B,0 SKIP IF B>A
                          MIC GRP,1H5621B,1 WRITE GRAPHICS
                          MIC ILP,1H5627B,4 WRITE ALPHA-NUMERICS INST.
                          MIC GET,1H5629B,3 GET DATUM
                          MIC WDW,1H5627B,1 WINDOW ADDER
                          MIC CMP,1H5607B,0 SKIP IF B>A
                          MIC SAD,1H5630B,1 ADD A TO DOUBLE WORD
                          MIC DAD,1H5631B,1 ADD A & B TO DOUBLE WORD
                          MIC WMV,1H5632B,2 RE-ENTRANT MVW
                          MIC FIL,1H5634B,1 FILTER
                          MIC IDN,1H5613B,0 IDENTIFY MICROCODE REVISION

NUPAC EQU *
    LOOP LDA ERFLG
         SZA
         HLT
         TSZ SECTR
         JMP NUNSC

LDA =D-125
         STA SECTR
         LDB PEAK
         ASR 5
         CMB,INM
```

```
 0040    00012 046057X       ADH PEAK
 0041    00013 002074R       LDA #04HM
 0042    00014 155007         CMP
 0043    00015 004050         LDB 0
 0044    00016 076057X       STH PEAK
 0045*
 0046*   QRS DETECTOR
 0047*
 0048    00017 155775  NONSC THS #0777 INDX
         00020 026075R
         00021 000027X
 0049    00022 016063X       JSR SCAN
 0050    00023 016026X       JSR GOSPL
 0051*
 0052    00024 006027X       LDA INDX
 0053    00025 010004         INA
 0054    00026 076027X       STA INDX
 0055    00027 015062X       JSR RWVSB
 0056    00030 026000R       JMP LOOP
 0057*
 0058    00031 010025X       JSR FPTSR       FIND FIDUCIAL POINT.
 0059    00032 076071R       STR TEMP3       OLD FID PNT
 0060    00033 072572R       STA TEMP4       NEW FID PNT
 0061    00034 007004         COR,INR
 0062    00035 046024X       ADB FPINX
 0063    00036 006020         SSR
 0064    00037 026042R       JMP RINV
 0065    00040 046076R       ADR #0-1000
 0066    00041 006021         SSR,RSS
 0067    00042 007401  RINV  CCR,RSS
 0068    00043 046077R       ADR #01000
 0069    00044 015020         RLS,PLS
 0070    00045 076061X       STR RTOR
 0071*
 0072*   CODE ADDED TO MAKE SURE THIS IS NOT T-WAVE
 0073*
 0074    00046 002000R       LDA #0350
 0075    00047 155007         CMP
 0076    00050 002001         RSS
 0077    00051 026060R       JMP NOTHV
 0078    00052 002071R       LDA TEMP3
 0079    00053 042001R       ADA #050
 0080    00054 072024X       STA FPINX       TEMPORARILY
 0081    00055 002047X       LDA NDTH1
 0082    00056 042001R       ADA #050
 0083    00057 016040X       JSR MSNAP
 0084    00060 006071R       LDR TEMP3       OLD ONE
 0085    00061 076024X       STR FPINX
 0086    00062 006062R       LDR #0200
 0087    00063 155007         CMP
 0088    00064 002001         RSS
 0089    00065 026561R       JMP RTONE
 0090    00066 002072R  NOTHV LDA TEMP4
 0091    00067 072024X       STA FPINX
 0092*
 0093*
 0094    00070 012010X       AND CSLEN
 0095    00071 032063R       IOR #010000M
 0096    00072 004000         LDB 0
 0097    00073 016054X       JSR OUTPT
 0098*
 0099    00074 016050X       JSR NOISH       CALCULATE NOISE
 0100*
 0101*   SELECT AND DISPLAY NORMAL BEAT
 0102*
 0103    00075 102001         LIA 1
 0104    00076 002021         SSR,RSS
 0105    00077 026104R       JMP NDISW
 0106    00100 002401         CLA
 0107    00101 112001         OTA 1
 0108    00102 072066R       STA LHNCT
 0109    00103 072067R       STA RHMAX
 0110    00104 025066R  NDSW LDA LHNCT
 0111    00105 052004R       CPA #014
 0112    00106 026151R       JMP CALCH
 0113    00107 056560R       ISZ LHNCT
```

```
0114   00111 025876       LDA RRMAX
0115   00111 06501X       LLR RTOR
0116   00112 1056?7       CMP
0117   00113 261519       JMP CALCW
0118   00114 072678       STA RRMAX
0119   00115 02247X       LDA NRTM1
0120   00116 016052R      JSR NSNAP
0121   00117 016021X      JSR ERASE
0122   00120 02247X       LDA NRTM1
0123   00121 016017X      JSR CSNAP
0124   00122 062012X      LDA RTOOT
0125   00123 072011X      STA RTRMN
0126   00124 025779       LDA #0100
0127   00125 072035X      STA RRTOR
0128   00126 056050       LDA #0100
0129   00127 016001X      JSR RTLGL
0130   00130 06203X       LDA RTCNT
0131   00131 072004X      STA BTCUT
0132   00132 002400       CLA
0133   00133 072034X      STA RRDEV
0134   00134 072074X      STA VFID
0135   00135 072073X      STA VCNT
0136   00136 072046X      STA NAGE
0137   00137 072067X      STA BCNT
0138   00140 105745       LLX NFMLY       CLEAR POPULATIONS
       00141 000074
0139   00142 105740 CLPLP SAX POP
       00143 000062X
0140   00144 105740       SAX AGE
       00145 000026X
0141   00146 105761       DSX
0142   00147 261022R      JMP CLPLP
0143   00150 265616       JMP BTDNE       BEAT DONE
0144*
0145   00151 016104X CALCW JSR WIDSH      CALCULATE WIDTH
0146*
0147*
0148*   CALCULATE MATCH
0149*
0150   00152 062047X      LDA NRTM1
0151   00153 016004,X     JSR RSNAP
0152   00154 072032X      STA MATCH
0153   00155 062001X      LDA NOISE
0154   00156 056005R      LDB #0512
0155   00157 105617       CMP
0156   00160 260470R      JMP NOUED
0157*
0158*   SEE IF VPB
0159*
0160   00161 025678R      LDA #0250       IF PREV BEAT NOISY
0161   00162 066017X      LDA RRATH       DON'T CALL THIS
0162   00163 056001R      CMB #0-1        ONE EARLY
0163   00164 262620R      JMP OFALT
0164   00165 062035X      LDA RRTOR
0165   00166 001121       ARS, ARS
0166   00167 001100       ARS
0167   00170 042034X      ADA RRDEV
0168   00171 072067X      STA TEMP1
0169   00172 062035X      LDA RRTOR
0170   00173 001040       CMA, INA
0171   00174 042001X      ADA RTOR
0172   00175 104240       MPY #0100
       00176 000114
0173   00177 104040       DIV TEMP1
       00200 000067X
0174   00201 042075R      ADA #0250
0175   00202 056012R      LDB #0125
0176   00203 105617       CMP
0177   00204 002001       RSS
0178   00205 062125       LDA #0125
0179   00206 066038X OFALT LDB MATCH
0180   00207 105617       CMP
0181   00210 260411R      JMP NUTV
0182   00211 061211X      LDB WIDTH       NO VPB'S NARROWER THAN 65 MSEC.
0183   00212 025015R      LDA #080
```

```
0154    00213 1.5607        CMP
0155    00214 126411R       JMP NOTV
0156*
0157*
0158*
0159*   FLM FOUND
0160*
0161*   FLM FAMILIES ARE EXAMINED IN DECENDING ORDER OF POPULATION TO
0162*   SEE IF ONE MATCHES THIS BEAT.
0163    00215 152573R       LDA NFMLY
0164    00216 016.66X       JSR SORT
0165    00217 0.241         CLA,RSS
0166    00220 052.7.X MTLUP LDA TEMP2
0167    00221 152573R       CPA NFMLY
0168    00222 126010R       JMP RPLCE
0169    00223 002304        INA
0170    00224 172173X       STA TEMP2
0171    00225 02,20X        ADA OTOFD
0172    00226 100000        LDA 0,I
0173    00227 072271X       STA FMLY
0174    00230 101741        CAX
0175    00231 101742        LAX POP
        00232 000063X
0176    00233 052.63        SZA,RSS
0177    00234 126010R       JMP RPLCE
0178    00235 1.1742        LAX SNPAD
        00236 000063X
0179    00237 016042X       JSB MSNAP
0210    00240 105745        LDA FMLY        IF THIS IS PREV BEAT,
        00241 000071X
0211    00242 000017R       LDA =02MM
0212    00243 1.5607        CMP
0213    00244 042220R       JMP MTLUP
0214    00245 101742        LAX SNPAD
        00246 000063X
0215    00247 005047X       LDA NATMI
0216    00250 016041X       JSR MSNSN
0217    00251 1.5735        LDX FMLY
        00252 000071X
0218    00253 000012R       LDA =0125
0219    00254 1.5607        CMP
0220    00255 126262R       JMP INPOP
0221    00256 002040        CLA
0222    00257 1.1742        SAX POP
        00260 000063X
0223    00261 125573R       JMP MTLUP
0224    00262 1.1742 INPOP LAX POP
        00263 000063X
0225    00264 002044        INA
0226    00265 02.20         SSA
0227    00266 052014R       LDA =H77777
0228    00267 1.174.        SAX POP
        00270 000063X
0229    00271 1.1742        LAX AGE
        00272 000063X
0230    00273 000016R       LDA =064
0231    00274 1.5607        CMP
0232    00275 126056R       JMP UPVPB       TOO LONG AGO
0233    00276 105742        LDX PATH
        00277 000056X
0234    00300 000012R       CPA =02
0235    00301 002001        RSS
0236    00302 126050R       JMP UPVPB
0237    00303 000017R       LDA =0=36
0238    00304 016072X       JSR LATER
0239    00305 1.1742 UPVPB LAX SNPAD        SNAP POINTER
        00306 000063X
0240    00307 016072X       JSR USNAP       UPDATE
0241*          LDA PPATH       IF PREVIOUS BEAT WAS
0242*          SZA,RSS         NORMAL, UPDATE R-R INTERVAL
0243*          JSR UPPR
0244    00310 002044        CLA,INA         MARK THIS BEAT
0245    00311 072.1X        STA PPATH       AS VPB
0246    00312 016050X       JSR CUVPB
0247    00313 000017R       LDA =0=36
```

```
0243   00314 015001X         JSR RTLBL
0244   00315 026502R         JMP IBAG2      TO SKIP TIC
0250*
0251*
0252*
0253*  REPLACE LEAST POPULOUS FAMILY
0254   00316 105745  RPLCE  LDX FMLY        INDEX
       00317 000071X
0255   00320 055490          CCA            SET AGE TO -1.
0256   00321 101740          SAX AGE        IT WILL BE INCED
       00322 000065X
0257   00323 002404          CLA,INA        MAKE POP 1
0258   00324 101740          SAX POP
       00325 000060X
0259   00326 002510R         LDA #02
0260   00327 101740          SAX PATH
       00330 000056X
0261   00331 072010X         STA PPATH
0262   00332 101742          LAX SNPAD      SNAP POINTER
       00333 000065X
0263   00334 015052X         JSR NSNAP      MAKE NEW SNAP
0264   00335 101742          LAX SNPAD
       00336 000065X
0265   00337 015017X         JSR DSNAP      DISPLAY IT
0266   00340 006024R         LDS #0-24      FLR.
0267   00341 015001X         JSR RTLBL
0268   00342 026502R         JMP IBAG2      TO SKIP TIC
0269*
0270*  SUBROUTINE TO UPDATE MEAN R-R INTERVAL
0271*
0272   00343 000002Z  UMRR   POP
0273   00344 002001X         LDA RTOR
0274   00345 042020          SSA
0275   00346 126343R         JMP UMRR,I
0276   00347 002035X         LDA PRTOR
0277   00350 003004          CLA,INA
0278   00351 042001X         ALA RTOR
0279   00352 072070X         STA TEMP2
0280   00353 001121          ARS,ARS
0281   00354 001100          ARS
0282   00355 042035X         ADA MRTOR
0283   00356 072035X         STA MRTOR
0284   00357 126343R         JMP UMRR,I
0285*
0286*  SEE IF COMPENSITORY PAUSE
0287*
0288   00360 002035X  PHPLR  LDA MRTOR
0289   00361 001121          ARS,ARS
0290   00362 001121          ARS,ARS        1/16 MEAN R TO R
0291   00363 042035X         ADA MRTOR      PLUS MEAN R TO R
0292   00364 042034X         ADA MRDEV
0293   00365 042034X         ADA MRDEV      PLUS 2 DEVIATION
0294   00366 006001X         LDS RTOR       IS R TO R BIGGER
0295   00367 1.5667          CMP
0296   00370 126442R         JMP NPATH      IF NO COMP PAUSE
0297*
0298   00371 105745          LDX NFMLY
       00372 000070R
0299   00373 101742  CPLUP  LAX AGE        FIND W AGE FAMILY
       00374 000065X
0300   00375 022073          SZA,RSS
0301   00376 026492R         JMP YVPH
0302   00377 105761          DSX
0303   00400 026373R         JMP CPLUP
0304   00401 026506R         JMP INAGE      ERROR!
0305   00402 105743  YVPH   STX FMLY
       00403 000071X
0306   00404 015055X         JSR DUVPB
0307   00405 002404          CLA
0308   00406 006175          LDA #0-36
0309   00407 015022X         JSR LGTLR      PUT TIC ON PREV BEAT
0310   00410 026422R         JMP CPRTN
0311*
0312*  UPDATE NORMAL BEAT
```

```
0013*
0014    00411  02'24X  NOTV   LDA FPTNX
0015    00412  72075X         STA VFTNX
0016    00413  02'13X         LDA BPATH
0017    00414  04304          CLA
0018    00415  72041X         STA APATH
0019    00416  02010K         CPA #02              PREV BEAT FLB?
0020    00417  26069K         JMP PRFLR
0021    00420  02002          SZA                  IF PREV BEAT NORMAL
0022    00421  02021K         CPA #01              OR VPB
0023    00422  16043K  CPRTN  JSB UARR             UPDATE MEAN R-R
0024    00423  02013X         LDA APATH            IF PREV BEAT NORMAL
0025    00424  06061X         LDB RTON             AND R-R DEFINED,
0026    00425  06021          SZB,RSS
0027    00426  02002          SZA                  THEN UPDATE MEAN DEV
0028    00427  26442K         JMP NPATH
0029    00430  06470X         LDA TEMP2
0030    00431  04020          SAM
0031    00432  07304          CMB,INB
0032    00433  02034X         LDA MRDEV
0033    00434  03004          CMA,INA
0034    00435  40001          ADA 1
0035    00436  01121          ARS,ARS
0036    00437  01101          ARS
0037    00440  42034X         ADA MRDEV
0038    00441  72034X         STA MRDEV
0039    00442  02032X  NPATH  LDA MATCH
0040    00443  4201DR         ADA #0-130
0041    00444  04404          CLB,INB
0042    00445  02022          SSA
0043    00446  07404          CCB
0044    00447  45049X         ADB RAGE
0045    00450  06v21          SZB,RSS
0046    00451  75040X         STA RAGE
0047    00452  02040X         LDA RAGE
0048    00453  12020H         CPY #01M
        00454  00004R
0049    00455  02022R         ADA #099
0050    00456  02032X         LDA MATCH
0051    00457  12007          CPB
0052    00460  02021          RSS
0053    00461  26050R         JMP IMAGE
0054*
0055*
0056    00462  02047X         LDA NRTM1            SNAP POINTER
0057    00463  16072X         JSB USNAP
0058    00464  02011X         LDA GTRAN
0059    00465  03004          CMA,INA
0060    00466  42012X         ADA MTDEF
0061    00467  01121          ARS,ARS
0062    00470  01121          ARS,ARS
0063    00471  02121          SSA,RSS
0064    00472  01121          ARS,ARS
0065    00473  42011X         ADA MTRAN
0066    00474  72011X         STA MTRAN
0067    00475  26050R         JMP IMAGE
0068    00476         NOUPD   NOP *
0069    00476  04004          CLA                  INDICATE NOISY BEAT
0070    00477  72013X         STA APATH
0071    00500  02023R  IMAGE  LDA #0-12
0072    00501  16001X         JSB BTLRL
0073    00502  10245  IAG2    LDX NFMLY            INC AGE OF EACH FLB
        00503  20057H
0074    00504  06024H         LDA #UACM
0075    00505  11142  IAGLP   LAX AGE
        00506  30040X
0076    00507  02204          INA
0077    00510  10067          CPA
0078    00511  02301          CLA,RSS              IF FAMILY IS
0079    00512  26010R         JMP ILUPR            SCRUB IT
0080    00513  11174          SAX PUP
        00514  30040X
0081    00515  11174  ILUPR   SAX AGE
        00516  30040X
0082    00517  10701          DSX
0083    00520  26050R         JMP IAGLP
```

```
0044    00521 0524278    LEA INOX        SEE HOW LONG THESE CALCULATIONS TOOK.
0045    00522 003084     CPA,INA
0046    00523 042825X    ALA FINDX
0047    00524 012114X    ADD BUFL
0048    00525 001420     ALS,ALS
0049    00526 072010X    STA DELAY
0050    00527 105740     LDX VRCNT
        00530 000076X
0051    00531 101742   VRLUP LDA VRPT
        00532 000077X
0052    00533 010010X    JSR RTOD
0053    00534 101742     CXA
0054    00535 104004     LEA 0
0055    00536 001000     ALS
0056    00537 044000     ALR 0
0057    00540 030044X    ALR MSPT3
0058    00541 002010     LDA =02
0059    00542 105032     MNV N2 1,1
        00543 000045X
        00544 100001
0060    00545 105761     PSK
0061    00546 020516     JMP VRLUP
0062    00547 052130X    LDA LINE1
0063    00550 055042X    LDB MSPT1
0064    00551 105740     LDX DSLN1
        00552 000035X
0065    00553 015000X    JSR ALSUB
0066    00554 052131X    LDA LINE2
0067    00555 055043X    LDB MSPT2
0068    00556 105740     LDX MSLN2
        00557 000037X
0069    00560 015000X    JSR ALSUB
0070    00561 002400   STONE CLA
0071    00562 006030X    LEA WHITE
0072    00563 072030X    STA WHITE
0073    00564 072031X    STA OLWHT
```

```
0001                    ASMB,R,L       REVISED    24 AUG 77
0002                    NAM RWAV       REVISED    24 AUG 77

PAGE  0001    PRGG TO HANDLE PACED PATTERNS, PLUS COMMON SUBS.   24 AUG 77

0004                    ENT START
0005                    ENT RTLGL,LBTLR,BTCNT,PTOUT
0006                    ENT AGE,ALSUB,BCNT,BPATH,BTBMN,BTOBT,BTOD,BUFL,DELAY
0007                    ENT DSLEN,DSNAP,DTORD,ERASE,ERFLG,FINDX,FPINX,FPTSB
0008                    ENT GUSPL,INOX,LINE1,LINE2,MATCH,MHITE,MROEV
0009                    ENT MRTOR,MSLN1,MSLN2,MSNAP,MSNSN,MSPT1,MSPT2,MSPT3
0010                    ENT N2,NAGE,NBTM1,NOISB,NOISE,NSNAP,OLMHT
0011                    ENT OUTPT,OUVPB,PATH,PEAK,POP,RTOR,RWVSB
0012                    ENT SCAN,SECTR,SNPAD,SORT,TEMP1,TEMP2,FMLY
0013                    ENT USNAP,VCNT,VFIB,VFINX,VRCNT,VRPT,WIDSB,WIDTH
0014                    EXT LINK,NOPAC
0015                    MIC ERS,145601B,4
0016                    MIC WRT,105600B,4
0017                    MIC GRP,105621B,1 WRITE GRAPHICS
0018                    MIC GET,105620B,3 GET DATUM
0019                    MIC CMP,105607B,0 SKIP IF B>A
0020                    MIC SAD,105630B,1 ADD A TO DOUBLE WORD
0021                    MIC BAD,105631B,1 ADD A & B TO DOUBLE WORD
0022                    MIC MNV,105632B,2 RE-ENTRANT MVW
0023                    MIC FIL,105634B,1 FILTER
0024                    MIC ION,105613B,0 IDENTIFY MICROCODE REVISION
0025*
0026*   INITIALIZATION
0027*
0028                    START LDA GVGID
0029    00001 102001    OTA 1
0030    00002 002679    LEA A/DIO
0031    00003 006000X   LDA PRDIO
```

```
0032   00004 102000         HLT 0
0033   00005 102110         SIF 108
0034   00006 072057R        STA A/OIO
0035   00007 076066R        STA PPDIO
0036   00010 102001         LIA 1
0037   00011 072065R        STA TEMP1
0038   00012 012066R        AND B77
0039   00013 072061R        STA GVGIO
0040   00014 115013         IFM
0041   00015 102001         LIA 1
0042   00016 062053R        LDA JSPEC
0043   00017 172057R        STA A/OIO,I
0044   00020 062061R        LDA GVGIO
0045   00021 032054R        IOR CLFW
0046   00022 172061R        STA GVGIO,I
0047   00023 065064R        LDB FWPRG
0048   00024 102001         RSS
0049   00025 105744  IOLUP  CXR
0050   00026 000004         IOR
0051   00027 005043R        CPB LWPRG
0052   00030 025065R        JMP INIT
0053   00031 101041         LDA 1,I
0054   00032 012072R        AND IOMSK
0055   00033 105741         CCX
0056   00034 006000         CLF
0057   00035 052040R        CPA A/OHL
0058   00036 006057R        LDB A/OIO
0059   00037 052041R        CPA PPOHL
0060   00040 006076R        LDB PPDIO
0061   00041 052042R        CPA GVGHL
0062   00042 006061R        LDB GVGIO
0063   00043 006003         SZB,RSS
0064   00044 026025R        JMP IOLUP
0065   00045 101742         LAX 0
       00046 000000
0066   00047 012063R        AND MDSC
0067   00050 106001         IOR 1
0068   00051 101744         SAX 0
       00052 000000
0069   00053 026025R        JMP IOLUP
0070 *
0071   00054 106100  CLFW   CLF 0
0072   00055 116001X JSBDC  JSB LINK,I
0073   00056 000077         OCT 77
0074   00057 000022  A/OIO  ABS A/O
0075   00060 000010  PPDIO  ABS PPD
0076   00061 000024  GVGIO  ABS GVG
0077   00062 172077  IOMSK  OCT 172077
0078   00063 177700  MDSC   OCT 177700
0079   00064 005064R FWPRG  DEF *
0080 *
0081   00065 103424  INIT   MIA GVG,C
0082   00066 102324         SFS GVG
0083   00067 025066R        JMP *-1
0084   00070 062625R        LDA CCONT
0085   00071 072001X        STA LINK
0086   00072 062745R        LDA TEMP1
0087   00073 001727         ALF,ALF
0088   00074 001222         RAL,RAL
0089   00075 012066R        AND B77
0090   00076 032575R        IOR DIGCN         FORM,DIG CONT WORD
0091   00077 102522         OTA A/O
0092   00100 016167R        JSB CLFW
0093   00101 017064R        JSB CONT
0094   00102 102100         SIF 0
0095 *
0096 * OPCALL PCAR
0097 *
0098   00103 026062X        JMP FOPAC
0099   00104          PACED EQU *
0100   00104 060015R LOOP   LDA ERFLG
0101   00105 002002         SZA
0102   00106 102000         HLT
0103   00107 036005R        ISZ SECTR
0104   00110 026125R        JMP NONSC
0105 *
```

```
0106    00111  03454R          LDA #0-125
0107    00112  072600R         STA SECTR
0108    00113  06567R          LDA PEAK
0109    00114  1 1025          ASR 5
0110    00115  07064           CMP,INR
0111    00116  045476          AIF PEAK
0112    00117  00257 R         LDA 0400
0113    00120  1 5067          CMP
0114    00121  04070           LLR 0
0115    00122  076567R         STA PEAK
0116*
0117*   QRS DETECTOR
0118*
0119    00123  1 5775  NONSC  TCA #0777 INDX
        00124  07355R
        00125  072622R
0120    00126  016537R         JSR SCAN
0121    00127  017155R         JSR GDSPL
0122*
0123    00130  066022R         LDA INDX
0124    00131  1 6664          TFR
0125    00132  076622R         STA INDX
0126    00133  017225R         JSR RAVSR
0127    00134  026144R         JMP LOOP
0128    00135  1 0250          LDA 1
0129    00136  1 0021          SSA,RSS
0130    00137  026147R         JMP OUFPT
0131    00140  1 5745          LDX RPMLY
        00141  02756R
0132    00142  02400           CLA
0133    00143  1 1740  CLLUP  SAR POP
        00144  05024R
0134    00145  1 5761          DSX
0135    00146  026143R         JMP CLLUP
0136*
0137    00147  017551R OUFPT  JSR FPTSR          FIND FIDUCIAL POINT.
0138    00150  07064           CMP,INR
0139    00151  046005R         ALP FPINX
0140    00152  06020           SSR
0141    00153  026156R         JMP RINV
0142    00154  047356R         ALO #0-1000
0143    00155  06021           SSS,RSS
0144    00156  07401    RINV  CCM,RSS
0145    00157  047357R         ACM #01000
0146    00160  05020           SLS,PLS
0147    00161  076656R         STR RTCR
0148    00162  012561R         ALO DSLEN
0149    00163  032623R         TOR FIRIT
0150    00164  04000           LLR 0
0151    00165  017173R         JSR OUTPT
0152*
0153    00166  017773R         JSR NOISR          CALCULATE NOISE
0154    00167  062653R         LDA NOISE
0155    00170  067466R         LDR #0512
0156    00171  1 5067          CMP
0157    00172  026317R         JMP NOUPD
0158*   FLR FOUND
0159*
0160*   FLR FAMILIES ARE EXAMINED IN DECENDING ORDER OF POPULATION TO
0161*   SEE IF ONE MATCHES THIS BEAT.
0162    00173  062756R         LDA RPMLY
0163    00174  016112R         JSR SORT
0164    00175  02401           CLA,RSS
0165    00176  072740R MTLUP  LDA TEMP2
0166    00177  027566R         CRA RPMLY
0167    00200  026260R         JMP RPLCE
0168    00201  00204           INA
0169    00202  072740R         STA TEMP2
0170    00203  021616R         ADA ETORD
0171    00204  160000          LDA 0,I
0172    00205  072661R         STA FRLY
0173    00206  1 1741          CAX
0174    00207  1 1742          LAX POP
        00210  05024R
0175    00211  02295           SZA,RSS
0176    00212  026266R         JMP RPLCE
```

```
0177   00213 101742         LAX SNPAD
       00214 027568
0178   00215 162678         JSR DSNAP
0179   00216 073618         LDB =0150
0180   00217 100007         CPP
0181   00220 026178         JMP RTLUP
0182   00221 072651R        STA PATCH
0183   00222 105745         LDX FMLY
       00223 020618
0184   00224 003400         CLA
0185   00225 101740         SAX AGE
       00226 055358
0186   00227 052758         LDA BPATH     IF PREV BEAT NOISY,
0187   00230 003603         CMA,SZA,RSS   DON'T UPDATE
0188   00231 026320R        JMP IMAGE
0189*  UPDATE R-R INTERVAL WITH 1/8 TIME CONSTANT
0190   00232 101742         LAX RRINT
       00233 055178
0191   00234 004400         LDB K
0192   00235 007004         CMB,INB
0193   00236 140658         ADB RTOR
0194   00237 005121         RES,RSS
0195   00240 005100         RSS
0196   00241 005021         SSA,RSS
0197   00242 004004         INB
0198   00243 001001         ADA 1
0199   00244 101740         SAX RRINT
       00245 055178
0200   00246 101742         LAX POP
       00247 050248
0201   00250 012004         INA
0202   00251 012000         SSA
0203   00252 003602R        LDA =B77777
0204   00253 101740         SAX POP
       00254 050248
0205   00255 101742         LAX SNPAD     SNAP POINTER
       00256 027568
0206   00257 016431R        JSR DSNAP     UPDATE
0207   00260 105745         LDX FMLY
       00261 020618
0208   00262 101742         LAX SNPAD
       00263 027568
0209   00264 017560R        JSR AFMSB
0210   00265 026320R        JMP IMAGE

0211*
0212*
0213*
0214* REPLACE LEAST POPULOUS FAMILY
0215   00266 052758 RPLCE LDA BPATH        IF PREV BEAT NOISY,
0216   00267 003603         CMA,SZA,RSS    DON'T UPDATE
0217   00270 026321R        JMP CLPTH
0218   00271 105745         LDX FMLY       INDEX
       00272 020618
0219   00273 002058R        LDA RTOR       INITIALIZE R-R
0220   00274 101740         SAX RRINT
       00275 055178
0221   00276 003400         CCA            SET AGE TO -1,
0222   00277 101740         SAX AGE        IT WILL BE INCED
       00300 055358
0223   00301 002404         CLA,INA        MAKE POP 1
0224   00302 101740         SAX POP
       00303 055248
0225   00304 003363R        LDA =02
0226   00305 101740         SAX PATH
       00306 050431R
0227   00307 072758R        STA BPATH
0228   00310 101742         LAX SNPAD      SNAP POINTER
       00311 027568
0229   00312 016518R        JSR NSNAP      MAKE NEW SNAP
0230   00313 101742         LAX SNPAD
       00314 027568
0231   00315 016461R        JSR DSNAP      DISPLAY IT
0232   00316 026320R        JMP IMAGE
0233   00317 003401 NOUPD   CCA,RSS
```

```
0234  0320 002061R  IVAGE LDA FMLY
0235  0321 072751R  CLPTH STA BPATH    ENTERED WITH A=0
0236  0322 105745         LDX NFMLY    INC AGE OF EACH FLB
      0323 002756R
0237  0324 007364R         LDB #0600
0238  0325 101742  IAGLP  LAX AGE
      0326 015036R
0239  0327 002004          INA
0240  0330 105007          CMP          IF FAMILY IS
0241  0331 002401          CLA,RSS      SCRUB IT
0242  0332 026035R         JMP ILUPR
0243  0333 101740          SAX PUP
      0334 015024R
0244  0335 101740  ILUPR  SAX AGE
      0336 015036R
0245  0337 105761         DSX
0246  0340 025325R         JMP IAGLP
0247  0341 102622R         LDA INDX    .SEE HOW LONG THESE CALCULATIONS TOOK.
0248  0342 003004          CHA,LDA
0249  0343 042017R         ADA PINDX
0250  0344 012565R         AND MUFL
0251  0345 001024          ALS,ALS
0252  0346 072645R         STA DELAY
0253  0347 105745         LDX VRCNT
      0350 002625R
0254  0351 101742  VRLUP LAX VRPT 0352  2044
0255  0353 017007R         JSM PTOU
0256  0354 101744         CXA
0257  0355 104060          LDB 0
0258  0356 005040          ALS
0259  0357 044000          ADB 0
0260  0360 046505R         ADB MSPT3
0261  0361 033636          LDA #02
0262  0362 105032          MLV N2 1,I
      0363 002737R
      0364 102401
0263  0365 105761          DSX
0264  0366 025051R         JMP VRLUP
0265  0367 102035R         LDA LINE1
0266  0370 006604R         LDB MSPT1
0267  0371 105745         LDX MSLN1
      0372 002735R
0268  0373 016437R         JSM ALSUB
0269  0374 002035R         LDA LINE2
0270  0375 006605R         LDB MSPT2
0271  0376 105745         LDX MSLN2
      0377 002735R
0272  0400 016437R         JSM ALSUB
0273  0401 002400          CLA
0274  0402 067012R         LDB PHITE
0275  0403 073012R         STA PHITE
0276  0404 076046R         STB DLPHT
0277  0405 026104R         JMP LUOP
0278*
0279*  SUBR TO UPDATE BEAT BUFFER
0280*
0281  0406 002000R  BTLOL NOP
0282  0407 002756R         LDA BTCNT
0283  0410 043553R         ADA #02
0284  0411 015005R         AND #576
0285  0412 072756R         STA BTCNT
0286  0413 002004          INA
0287  0414 042770R         ADA BTBUF
0288  0415 174000          STA 0,I
0289  0416 043566R         ADA #0=1
0290  0417 005005R         LDB PPINX
0291  0420 174000          STB 0,I
0292  0421 126416R         JMP BTLOL,I
0293*
0294  0422 002000R  LBTLH NOP
0295  0423 003524          CMA,CCE,INA
0296  0424 021020          ELA
0297  0425 002756R         ADA BTCNT
```

```
0288   00326 013567R          AND =B77
0289   00327 042770R          ALA PTBUF
0290   00430 174000           STB 0,I
0291   00431 126422R          JMP LATLR,I
0312*
0303*
0304*   SUBROUTINE TO ERASE GVG
0305*

0306   00432 000000   ERASE NOP
0307   00433 103424         CLA GVG,C
0308   00434 102324         SFS GVG
0309   00435 026434R        JMP *-1
0310   00436 126432R        JMP ERASE,I
0311*
0312*   SUBROUTINE TO WRITE CHARACTERS ON GVG
0313*
0314   00437 000000   ALSUB NOP
0315   00440 135761         LDX
0316   00441 072743R        STA LOCSC
0317   00442 003400         CCA
0318   00443 020400         CLR,ELB
0319   00444 103024         OTA GVG,C
0320   00445 102224         SFC GVG
0321   00446 026507R        JMP INMDA
0322   00447 135761   LLUP  DSX
0323   00450 032001         RSS
0324   00451 126437R        JMP ALSUB,I
0325   00452 135763         LDT
0326   00453 012551R        ADA BN40
0327   00454 072550R        STA CHAR
0328   00455 012556R        AND B77
0329   00456 032550R        CPA CHAR
0330   00457 002001         RSS
0331   00460 026447R        JMP LLUP
0332   00461 102124         STF GVG
0333   00462 106724         CLC GVG
0334   00463 002464         CLA,INA
0335   00464 103024         OTA GVG,C
0336   00465 105001         ERS PUNCT CHAR STC LOCSC
       00466 007140R
       00467 002550R
       00470 002537R
       00471 027743R
0337   00472 102124         STF GVG
0338   00473 106724         CLC GVG
0339   00474 002400         CLA
0340   00475 103024         OTA GVG,C
0341   00476 105000         WRT PUNCT CHAR STC LOCSC
       00477 007140R
       00500 002550R
       00501 002537R
       00502 027743R
0342   00503 102743R        LDA LOCSC
0343   00504 012637R        ADA C6
0344   00505 072743R        STA LOCSC
0345   00506 026447R        JMP LLUP
0346   00507         INMDA EQU *
0347   00507 135761   MLUP  DSX
0348   00510 032001         RSS
0349   00511 126437R        JMP ALSUB,I
0350   00512 135763         LDT
0351   00513 012551R        ADA BN40
0352   00514 072550R        STA CHAR
0353   00515 012556R        AND B77
0354   00516 032550R        CPA CHAR
0355   00517 002001         RSS
0356   00520 026507R        JMP MLUP
0357   00521 105001         ERS PUNCT CHAR SFC LOCSC
       00522 007140R
       00523 002550R
       00524 002412R
       00525 012743R
0358   00526 105000         WRT PUNCT CHAR CLF LOCSC
       00527 007140R
```

```
                                      LDA LOCSC
                                      ADA DC
                                      STA LOCSC
                                      JMP MLUP
*
*   SUBROUTINE TO SCAN BUFFER FOR VFIB ETC.
*
                        SCAN          NOP
                                      LDA FINDX         LOOP COUNTER
                                      STA VFINX
                                      CPY
                                      GET FINDX RATE ERROR

STA TEMP1         INITIAL SAMPLE TO FIND DIFF'S
                                      CLA               INITIALIZE ACCUMULATORS
                                      STA DTMP3
                                      STA DTMP3+1
                                      STA DTMP4
                                      STA DTMP4+1
                        WLUP          DSY               ADVANCE BACKWARDS
                                      NOP               MIGHT SKIP
                                      CYB               NEXT SAMPLE
                                      GET FINDX RATE DOWN

CAX               SAVE SAMPLE IN X
                                      LDB TEMP1
                                      STA TEMP1
                                      CBA,INA
                                      ALA 1             FIRST DIFFERENCE
                                      SSA
                                      CBA,INA           ABS VALUE
                                      CLR
                                      DAD DTMP3         ACCUMULATE

DST DTMP3

CXA               GET SAMPLE BACK
                                      SSA
                                      CBA,INA           ABS VALUE
                                      CLR
                                      DAD DTMP4         ACCUMULATE

DST DTMP4

JMP WLUP
*
                        WDUN          NOP
                                      DLD DTMP4

ASR 9
                                      STA SCAMP
                                      LDB BTMN
                                      CMP               IF SCAMP < BTMN
                                      RSS               THEN ASYSTOLE
                                      JMP REDAL
                                      DLD DTMP3

ASR 9             DIVIDE DENOMINATOR BY 512
                                      STA TEMP1
                                      DLD DTMP4

DIV TEMP1

MPY =D22

CLE
                                      ADA =D896
                                      SEZ
                                      INB
```

```
0417  00040 140490          DIV 01792
      00041  07072R
0418  00042  03404          CMA,INA
0419  00043 072050R         STA PHASE
0420  00044 007573R         LDA #D=32        A=PI/(2**)
0421  00045 1:5067          CMP
0422  00046 126537R         JMP SCAN,I       FREQ TOO HIGH
0423  00047 007374R         LDA #D=128
0424  00050 1:5067          CMP
0425  00051  02001          NSS
0426  00052 126537R         JMP SCAN,I       FREQ TOO LOW
0427  00053 007017R         LDA FINDX
0428  00054 1:5751          CPY
0429  00055  02400          CLA
0430  00056 072012R         STA CTMP3
0431  00057 072013R         STA CTMP3+1
0432  00060 072014R         STA CTMP4
0433  00061 072015R         STA CTMP4+1
0434  00062 1:5771  VFLUP   ISY
0435  00063 0:0028          NOP
0436  00064 1:5754          CYB
0437  00065 1:5020          GET FINDX HATE VFDUN
      00066 0:4017R
      00067 002445R
      00070 007319
0438  00071 072045R         STA TEMP1
0439  00072  40050R         ADD PHASE
0440  00073 1:5020          GET FINDX HATE VFDUN
      00074 0:4017R
      00075 022450
      00076 007319
0441  00077 072045R         STA TEMP2
0442  00100  03004          CMA,INA
0443  00101 1:3101          CLO
0444  00102 042045R         ADA TEMP1
0445  00103 002026          SSA
0446  00104 0:3004          CMA,INA
0447  00105 1:2201          SUC
0448  00106  03004          CMA,INA
0449  00107  02400          CLA
0450  00110 1:5031          HAD CTMP4
      00111  02014R
0451  00112 1:4401          BST CTMP4
      00113 002014R
0452  00114 002045R         LDA TEMP1
0453  00115 00074RR         LDA TEMP2
0454  00116  02026          SSA
0455  00117 0:3004          CMA,INA
0456  00120 000020          SSE
0457  00121  07004          CMA,INA
0458  00122 040001          ADA 1
0459  00123 0:6405          CLA
0460  00124 1:5031          HAD CTMP3
      00125  02012R
0461  00126 1:4401          BST CTMP3
      00127 002012R
0462  00130 026629         JMP VFLUP
0463  00131 000000  VFDUN   NOP
0464  00132 1:4200          OLD CTMP3
      00133 002012R
0465  00134 141031          ASR 9
0466  00135 072045R         STA TEMP1
0467  00136 1:4200          OLD CTMP4
      00137 002014R
0468  00140 140490          DIV TEMP1
      00141 072045P
0469  00142 072054R         STA VFRTC
0470  00143 007570R         LDA #D350
0471  00144 1:5067          CMP
0472  00145 126537R         JMP SCAN,I
0473  00146 1410000R        TSZ VFIS
0474  00147 0:0020          NOP
0475  00150 007055R  PEDAL  LDA #D=1068
0476  00151  02400          CLA
0477  00152 014422R         JSM LMTLH
0478  00153 126537R         JMP SCAN,I
```

```
0478*
0479*     SUBROUTINE TO MARK A VPB
0480*
0481  00704 000000  OUVPB NOP
0482  00705 002645R       LDA FPINX      PUT FIDUCIAL POINT
0483  00706 012561R       AND DSLEN      SCOPE LOCATION IN B
0484  00707 033678R       TCM #011       TO MARK 1, OR 2 VPB'S.
0485  00710 004000        LLB 0
0486*
0487  00711 002652R MOVPB LLA VCNT       INC V COUNT
0488  00712 002004        INA
0489  00713 002021        SSA,RSS
0490  00714 022652R       STA VCNT
0491  00715 047377R       ALR #0400      TIC 1 DOT ABOVE FIDUCIAL TIC
0492  00716 105745        LCX FMLY       SEE IF THIS IS FLB
      00717 002661R
0493  00720 101742        LAX PATH       FAMILY.
      00721 005031R
0494  00722 053400R       CPA #01        IF VPB FAMILY, LEAVE.
0495  00723 027142R       JMP MARKV
0496  00724 002004        CLA,INA        IF FLB, CHANGE TO VPB
0497  00725 101740        SAX PATH
      00726 005031R
0498  00727 002750R       LDA PPATH      IF THIS BEAT VPB
0499  00730 053400R       CPA #01
0500  00731 027061R       JMP MOVPB      GO AGAIN.
0501  00732 017173R MARKV JSB OUTPT      PUT DOT ON VIDEO
0502  00733 003400        CCA            AGE WILL BE INC
0503  00734 101740        SAX AGE        TO ZERO
      00735 005036R
0504  00736 126754R       JMP OUVPB,I
0505*
0506*     SUBROUTINE TO CONVERT BINARY NUMBER TO UP TO 6 DIGITS OF ASCII
0507*
0508  01007 000000  BTOD  NOP
0509  01010 065556R       LCB DN999
0510  01011 105607        CMP
0511  01012 002001        RSS
0512  01013 002550R       LDA DN999
0513  01014 065556R       LCB DN999
0514  01015 105607        CMP
0515  01016 002550R       LDA DN999
0516  01017 066044R       LCB BASE
0517  01020 076737R       STB R2
0518  01021 076740R       STB R3
0519  01022 003400        CLA
0520  01023 076742R       STB BDCTR
0521  01024 002021        SSA,RSS
0522  01025 027031R       JMP *+3
0523  01026 003404        CPA,INA
0524  01027 066643R       LCB NGLT
0525  01030 076642R       STB SIGN
0526  01031 003400  POLUP CLA
0527  01032 106400        DIV C10
      01033 062744R
0528  01034 072745R       STA TEMP1
0529  01035 062742R       LDA BDCTR
0530  01036 042003R       ALA OM1
0531  01037 072742R       STA BDCTR
0532  01040 046751R       ALB R2B
0533  01041 002011        SLA,RSS
0534  01042 005727        RLF,RLF
0535  01043 001150        ARS
0536  01044 042741R       ALA CN
0537  01045 144100        ADB C,I
0538  01046 174000        STB B,I
0539  01047 002745R       LDA TEMP1
0540  01050 002002        SZA
0541  01051 027031R       JMP POLUP
0542  01052 062742R       LDA BDCTR
0543  01053 042003R       AUA OM1
0544  01054 066642R       LDB SIGN
0545  01055 002011        SLA,RSS
0546  01056 005727        RLF,RLF
0547  01057 001150        ARS
0548  01060 042741R       ADA CN
```

```
1050    11001 144000         ALB H,I
1051    11002 174000         STA M,I
1052    11003 127007R        JMP FTOU,I
0053*
0054*   A/D DRIVER WHICH USES IP221 AS PACER
0055*
0056    11004 000000 CONT    NOP
0057    11005 072026R        STA SA      SAVE REGS
0058    11006 076027R        STB SB
0059    11007 115745         STX SX
        11070 002030R
0060    11071 105755         STY SY
        11072 002031R
0061    11073 001520         ERA,ALS
0062    11074 102201         SOC
0063    11075 002004         INA
0064    11076 072032R        STA SEO
0065    11077 063013R        LDA BFCNT   ADVANCE BUFFER COUNT
0066    11100 002004         INA
0067    11101 073015R        STA BFCNT
0068    11102 012506R        AND BUFL
0069    11103 042752R        ADA ADBUF   POINTER FOR DATA
0070    11104 106022         LIB A/D     DATA IS WAITING SINCE A/D FAST
0071    11105 006121         HRS,HRS
0072    11106 006121         HRS,HRS
0073    11107 174006         STB M,I     STORE IN CIRCULAR BUFFER
0074    11110 105634         FIL FLADR,I
        11111 002031R
0075    11112 052767R        LDA BTOUT
0076    11113 042776R        ADA BTBUF
0077    11114 056017R        LDA FINDX   TIME FOR NEW TIC?
0078    11115 147401R        ADE =D-125M
0079    11116 104006         CMR 0,I
0080    11117 127145R        JMP NWCNT   YES
0081    11120        LEVC    EQU *
0082    11120 062572R        LDA OUTCT
0083    11121 002003         SZA,HSS
0084    11122 127120R        JMP OTA
0085    11123 002004         INA
0086    11124 072572R        STA OUTCT
0087    11125 062573R        LDA OUTBD
0088    11126 102010  OTA    OTA PRO
0089    11127 062032R        LDA SEO     RESTORE REGS
0090    11130 100101         CLO
0091    11131 100030         SLA,ELA
0092    11132 102101         STO
0093    11133 062026R        LDA SA
0094    11134 066027R        LDB SB
0095    11135 105745         LDX SX
        11136 002030R
0096    11137 105755         LDY SY
        11140 002031R
0097    11141 103722         STC A/D,C   START NEXT CONVERSION
0098    11142 127004R        JMP CONT,I  RETURN
0099    11143 002004 NWCNT   INA
0100    11144 104000         LDB A,I
0101    11145 052572R        LDA OUTCT
0102    11146 105007         CMP
0103    11147 076572R        STA OUTCT
0104    11150 062767R        LDA BTOUT
0105    11151 043303R        ADA =02
0106    11152 013303R        AND =076
0107    11153 072767R        STA BTOUT
0108    11154 027120R        JMP LEVC
0109*
0110*
0111*   OUTPUT FIXED TRACE IN 8 POINT BLOCKS
0112*
0113    11155 000000 GOSPL   NOP
0114    11155 006022R        LDB INDX
0115    11157 105020         GET FINDX RATE ERROR
        11160 004017R
        11161 002243R
        11162 002257R
0116*
0117    11163 042623R        ADA HIBIT
```

```
0010   01104 012024R        AND H1774
0019   01105 064494         LDB 0
0020   01106 002022R        LDA INDX
0021   01107 012561R        AND OSLEN
0022   01170 044000         ALF 0
0023   01171 017173R        JSB OUTPT
0024   01172 127155R        JMP GOSPL,I
0025*
0026*  SUBROUTINE TO OUTPUT WAVEFORM
0027*
0028   01173 060000  OUTPT  NOP
0029   01174 002560R        LDA OSCNT
0030   01175 002004         INA
0031   01176 012561R        AND OSLEN
0032   01177 072560R        STA OSCNT
0033   01200 042753R        ADA OSPNT
0034   01201 174000         STB 0,I
0035   01202 002560R        LDA OSCNT
0036   01203 012562R        AND H7
0037   01204 022562R        CPA H7
0038   01205 002301         CCE,RSS
0039   01206 127173R        JMP OUTPT,I
0040   01207 002560R        LDA OSCNT
0041   01210 002004         INA
0042   01211 012561R        AND OSLEN
0043   01212 042753R        ADA OSPNT
0044   01213 006564R        LDB DMH
0045   01214 016260R        JSB GRPIC
0046*
0047   01215 002560R        LDA OSCNT
0048   01216 042563R        ADA OM7
0049   01217 012561R        AND OSLEN
0050   01220 042753R        ADA OSPNT
0051   01221 006564R        LDB DMB
0052   01222 000041         CLE
0053   01223 016260R        JSB GRPIC
0054   01224 127173R        JMP OUTPT,I
0055*
0056*  SUBROUTINE TO FLIP R-WAVES
0057*
0058   01225 060000  RWVSB  NOP
0059   01226 105020         GET FINDX WAVE ERROR
       01227 004017R
       01230 002245R
       01231 002250R
0060   01232 006570R        LDB LSINP    PREVIOUS VOLTS
0061   01233 076745R        STB TEMP1
0062   01234 007064         CMA,INA
0063   01235 072576R        STA LSINP    SAVE FOR NEXT TIME
0064   01236 040001         ADA 1        FIRST DIFFERENCE
0065   01237 006577R        LDB LSOLT
0066   01240 072577R        STA LSOLT    SAVE
0067   01241 222745R        XOR TEMP1    IF DERIVATIVE POS, THEN
0068   01242 002021         SSA,RSS      VOLTS SHOULD BE NEG
0069   01243 027254R        JMP LUOPR    AND VICE VERSA
0070   01244 002577R        LDA LSOLT
0071   01245 026001         XOR 1
0072   01246 002021         SSA
0073   01247 027314R        JMP PKFND
0074   01250 026062R LUOPR  LDA TWAVE   IN PQRST?
0075   01251 002004         INA
0076   01252 002020         SSA
0077   01253 072062R        STA TWAVE
0078   01254 007012R        LDB WHITE
0079   01255 000062         SZB
0080   01256 002020         SSA
0081   01257 127225R        JMP RWVSB,I
0082*         LDA PTOR
0083*         CMA,INA
0084*         ADA PRTOR
0085*         SSA
0086   01260 002400         CLA
0087   01261 040024R        ADA PRTOR
0088   01262 072745R        STA TEMP2
0089   01263 002022R        LDA INDX
```

```
1690   01204  003004            CMA,INA
4691   01205  042005R           ALA FPINX
4692   01206  064000            LDH 0                GET 5/8 TIMES TIME
4693   01207  001404            ALS                  FROM PREV FID PNT
1694   01270  046001            ADA 1                IN A REG
4695   01271  074022R           LDB *D-1540
4696   01272  105007            CMP
4697   01274  002021            SSA,RSS
4698   01275  127305R           JMP IBCNT
4699   01276  042740R           ADA TEMP2
0701   01277  100520            MPY OLPHT
       01300  025068R
4712   01301  100400            DIV TEMP2
       01302  027468R
4703   01303  067012P           LDA WHITE
4704   01304  105007            CMP
4705   01305  127225R           JMP RWVSB,I          NO
4706*         STAT RESETS
0707   01306  002047R  IBCNT   LDA CCNT
4708   01307  002004            INA
4709   01310  002021            SSA,RSS
4710   01311  072047R           STA CCNT
4711   01312  037225R           ISZ RWVSB
4712   01313  127225R           JMP RWVSB,I
0713   01314  062745R  PKFND   LDA TEMP1
4714   01315  002021            SSA,RSS
4715   01316  003004            CMA,INA
4716   01317  072745R           STA TEMP1
4717   01320  065067R           LDA PEAK
4718   01321  040001            ADA 1
4719   01322  000121            RRS,PKS
4720   01323  001004            BRS                  1 R PEAK IS R THRESHOLD
4721   01324  003024            CMA,SSA,INA
4722   01325  027332R           JMP RWAV?
4723   01326  105007            CMP
4724   01327  006001            LDA 1
4725   01330  042067R           ADA PEAK
4726   01331  072067R           STA PEAK
4727*
4728   01332  046745R  RWAV?   ADB TEMP1
4729   01333  006021            SSB,RSS
4730   01334  027253R           JMP LOOPR
4731   01335  066745R           LDB TEMP1
4732   01336  007004            CMB,INB
4733   01337  004065            CLE,ERB              MAKE EXPLICITLY POSITIVE
4734   01340  063012P           LDA WHITE
4735   01341  105007            CMP
4736   01342  027250R           JMP LOOPR
4737   01343  077012P           STB WHITE
4738   01344  062226R           LDA INDX
4739   01345  072574R           STA FSTR             PRELIMINARY FIDUCIAL POINT
1740   01346  062021R           LDA TWAIT
0741   01347  072002P           STA TWAVE
0742   01350  127225R           JMP RWVSB,I
0743*
0744*  THE FOLLOWING CODE CALCULATES THE FIDUCIAL POINT OF A QRS. FSTR POINTS
0745*  TO THE OUTPUT OF THE QRS DETECTOR AND IS THE HIGHEST ABSOLUTE PEAK OF
0746*  THE QRS. USING FSTR AS AN ORIGIN THIS SUBROUTINE FINDS THE NUMBER OF
0747*  SAMPLES TO THE FIDUCIAL POINT, CORRECTS FSTR, AND STORES THE RESULT IN
0748*  FPIDX. THE FIDUCIAL POINT IS THE CENTER OF GRAVITY OF THE DERIVITIVE
0749*  SQUARED:
0750*
0751*  FPIDX = FSTR + (SIGMA(N*(V(N)-V(N-1))↑2])/(SIGMA[V(N)-V(N-1))↑2])
0752*
0753*  WHERE N IS THE DIFFERENCE (IN 4 MSEC INCREMENTS) OF THE SAMPLE NUMBER
0754*  OF V AND FSTR, AND V(N) IS THE ECG VOLTAGE AT N + FSTR. ABSTM = ABS(N).
0755*  N ASSUMES VALUES FROM -37 TO +37. INTEGRATION STARTS AT FSTR AND
0756*  PROCEEDS SYMETRICALLY SUMMING A TERM TO THE LEFT AND ONE TO THE RIGHT
0757*  OF FSTR INTO A NUMERATOR ACCUMULATOR AND A DENOMINATOR ACCUMULATOR ON
0758*  EACH CIRCUIT OF THE LOOP BELOW.
0759*
0760*  MACRO "JET" RETURNS A SAMPLE VOLTAGE IN A REGISTER AT TIME SPECIFIED
0761*  IN B REGISTER.
0762*  MACRO "DAD" RETURNS IN A AND B REGISTERS THE SUM OF 32 BIT ARGUEMENT
0763*  AND ORIGINAL 32 BIT NUMBER IN A AND B. IF ADDITION CAUSES OVERFLOW,
```

0760* THEN RESULT IS DIVIDED BY 2 AND OVERFLOW BIT IS SET, OTHERWISE OVER-
0761* FLOW BIT IS CLEARED.
0762  01351 0060006  FPTSR  NOP
0763  01352 002404         CLA            CLEAR NUMERATOR
0764  01353 072626R        STA DTMP6
0771  01354 072621R        STA DTMP6+1
0771  01355 006574R        LDA FSTR       GET V(0)
0772  01356 105020         GET FINDX WATE ERROR
       01357 004017R
       01360 002245R
       01361 002250R
0773  01362 072633R        STA INPT1      SAVE TO CALC V(1)-V(0) AND V(0)-V(-1)
0774  01363 047360R        ADA #0-1       GET V(-1)
0775  01364 105020         GET FINDX WATE ERROR
       01365 004017R
       01366 002245R
       01367 002250R
0776  01370 072634R        STA INPT2      SAVE TO CALC V(-1)-V(-2)
0777  01371 103004         CMA,INA        REVERSE SIGN
0778  01372 042633R        ADA INPT1
0779  01373 100206         MPY 0          (V(0)-V(-1))↑2
       01374 006000
0780  01375 104450         DST DTMP5      INITIALIZE NUMERATOR
       01376 002610R
0781  01377 006464         CLE,INB        B <= 1
0782  01400 075041R        STB ABSTN      INITIALIZE ABS(N)
0783  01401 076027R        STB NCNT5      INITIALIZE DENOMINATOR OVERFLOW COUNTER
0784  01402 076027R        STB NCNT6      INITIALIZE NUMERATOR OVERFLOW COUNTER
0785  01403 006574R CNLUP  ADA FSTR       GET V(ABS(N)) TO RIGHT OF FSTR
0786  01404 105020         GET FINDX WATE ERROR
       01405 004017R
       01406 002245R
       01407 002250R
0787  01410 006633R        LDA INPT1
0788  01411 072633R        STA INPT1      STORE V(ABS(N)) FOR NEXT PASS
0789  01412 007104         CMA,INB        CHANGE SIGN
0790  01413 040001         ADA 1          DIFF FROM LEFT HAND NEIGHBOR
0791  01414 100206         MPY 0          DIFF↑2
       01415 006000
0792  01416 104450         DST DTMP4      SAVE IN TEMP LOCATION
       01417 002614R
0793  01420 006041R        LDA ABSTN      ABS(N)
0794  01421 007054         CMB            -ABS(N)-1
0795  01422 046574R        ADB FSTR       GET V(-ABS(N)-1) TO LEFT OF FSTR
0796  01423 105020         GET FINDX WATE ERROR
       01424 004021R
       01425 002245R
       01426 002250R
0797  01427 006634R        LDA INPT2
0798  01430 072634R        STA INPT2      STORE V(-ABS(N)-1) FOR NEXT PASS
0799  01431 007004         CMA,INA        CHANGE SIGN OF RIGHT HAND NEIGHBOR V
0800  01432 140261         ADA 1          DIFF FROM RIGHT HAND NEIGHBOR
0801  01433 100206         MPY 0          DIFF↑2
       01434 006000
0802  01435 104450         DST DTMP2      SAVE IN TEMP LOCATION
       01436 002610R
0803  01437 105031         DAD DTMP4      ADD TO DIFF↑2 FROM RIGHT OF FSTR
       01440 002614R
0804*
0805  01441 105745         LDX NCNT5      DIV BY 2 ONCE FOR
       01442 002020R
0806  01443 002001         RSS            EACH OVERFLOW OF DENOMINATOR
0807  01443 101721         ASR 1
0808  01445 105761         DSX
0809  01446 027444R        JMP *-2
0810*
0811  01447 105031         DAD DTMP5      ACCUMULATE INTO DENOMINATOR
       01450 002610R
0812  01451 104450         DST DTMP5
       01452 002610R
0813  01453 102201         SOC            DID ADDITION OVERFLOW?
0814  01454 036027R        ISZ NCNT5      YES, INC OVERFLOW COUNTER
0815  01455 104260         DLD DTMP2      GET DIFF↑2 FROM LEFT OF FSTR
       01456 002610R
0816  01457 003134         CMA,CLE,INA    CHANGE ITS SIGN
0817  01460 027040         CMB,SEZ

```
4010   01401  016004          INA
0015*
0020   01402  105631          OAD DTMP4      ADD TO DIFF+2 FROM RIGHT OF FSTR
       01403  012014R
0021*  THIS BLOCK MULTIPLIES 2 WORD INTEGER IN A AND B TIMES ABSTM
0022   01404  002020          SSA
0023   01405  016034          INA
0024   01406  076745R         STA TEMP1
0025   01407  100200          MPY ABSTM
       01410  020041R
0026   01411  144000          DST DTMP2
       01412  002010R
0027   01413  002745R         LDA TEMP1
0028   01414  100200          MPY ABSTM
       01415  020041R
0029   01416  004000          LLR 2
0030   01417  002400          CLB
0031   01420  105031          OAD DTMP2
       01421  012010R
0032*
0033   01422  135745          LDX NCNT6      DIVIDE BY 2 ONCE FOR EACH
       01423  020077R
0034   01424  002001          RSS            OVERFLOW OF NUMERATOR
0035   01425  101021          ASR 1
0036   01426  105761          ISX
0037   01427  027305R         JMP *-2
0038*
0039   01430  105031          OAD DTMP6      ACCUMULATE IN NUMERATOR
       01431  020205R
0040   01432  144000          DST DTMP6
       01433  020205R
0041   01434  102201          SOC            ADDITION CAUSED OVERFLOW?
0042   01435  036077R         ISZ NCNT6      YES, INC OVERFLOW COUNT
0043   01436  036041R         ISZ ABSTM      INC ABS(N)
0044   01437  006041R         LDR ABSTM
0045   01440  056071R         CPB DSB
0046   01441  002001          RSS            INTEGRATIONS DONE?
       01441                                 YES
0047   01442  027405R         JMP CNLUP      NO
0048   01443  144200          OLD DTMP5      DIVIDE DENOMINATOR BY 2 ENOUGH TIMES
       01444  020015R
0049   01445  101021  FNLUP   ASR 1          SO THAT IT FITS IN SINGLE WORD
0050   01446  036060R         ISZ NCNT5      INC NCNT5 EACH TIME
0051   01447  002021          SSA,RSS
0052   01450  066002          SZB
0053   01451  027525R         JMP FNLUP
0054*
0055   01452  072745R         STA TEMP1      SAVE SCALED DENOMINATOR
0056   01453  000060R         LDB NCNT5      NOW DIVIDE NUMERATOR BY 2 AS
0057   01454  007004          CLA,INB        MANY TIMES AS DENOMINATOR HAS BEEN
0058   01455  040077R         ADB NCNT6      DIVIDED - LESS THE NUMBER OF TIMES
0059   01456  006021          SSB,RSS        NUMERATOR HAS ALREADY BEEN DIVIDED
0060   01457  102000          HLT 0          COULDN'T BE POS
0061   01460  105741          CBX
0062*
0063   01461  144200          OLD DTMP5
       01462  020205R
0064   01463  101021          ASR 1
0065   01464  105761          ISX
0066   01465  027543R         JMP *-2
0067   01466  100400          DIV TEMP1      DIV BY SCALED DENOMINATOR
       01467  002745R
0068*  IF B POS, THEN FIDUCIAL POINT CORRECTION IS REDUCED BY 0.5 ON
0069*  AVERAGE DUE TO TRUNCATION. IF B NEG, THEN FIDUCIAL POINT CORRECTION
0070*  IS INCREASED BY 0.5 BY TRUNCATION. FOR EITHER SIGN WE WISH TO REDUCE
0071*  IT BY 0.5 SINCE BACKWARDS DIFFERENCES ARE USED ABOVE.
0072   01470  006002          SSB            B CONTAINS REMAINDER
0073   01471  143566R         ADA =0-1
0074   01472  042074R LVFPT   ADA FSTR
0075   01473  006065R         LDB FPIDX      A=NEW FIDUCIAL POINT  B=PREVIOUS ONE
0076   01474  072605R         STA FPIDX
0077   01475  127331R         JMP FPTSB,I    RETURN
0078*
0079*
0080*  COMPUT OF INERTIA OF ABS VAL OF DERIVATIVES OF GRS ABOUT FIDUCIAL POINT =
0081*
0082*  SIGMA[N*(ABS DV(N) + ABS DV(-N))] / SIGMA[ABS DV(N) + ABS DV(-N)]
```

```
4844*
4849* WIDTH = MOMENT OF INERTIA
4850*
4887  01556 x58580   WFMSB NOP
4888  01557 0434v3R        ALA =026
4889  01560 072747R        STA TEMP3
4890  01561 160v0C         LDA M,I
4891  01562 072633R        STA INPT1
4892  01563 072634R        STA INPT2
4893  01564 042404         CLA
4894  01565 072616R        STA DTMP5
4895  01566 072617R        STA DTMP5+1
4896  01567 072620R        STA DTMP6
4897  01570 072621R        STA DTMP6+1
4898  01571 056404         CLB,INB
4899  01572 076641R        STA ABSTH
4900  01573 046747R  WDLP  ADA TEMP3
4901  01574 150001         LDA 1,I
4902*
4903  01575 066033R        LDB INPT1
4904  01576 072633R        STA INPT1
4905  01577 047004         CMB,INB
4906  01600 040001         ADA 1
4907  01601 002420         SSA
4908  01602 043004         CMA,INA
4909  01603 072745R        STA TEMP1
4910*
4911  01604 066041R        LDB ABSTH
4912  01605 047004         CMB,INB
4913  01606 046747R        ADA TEMP3
4914  01607 150001         LDA 1,I
4915*
4916  01610 066034R        LDB INPT2
4917  01611 072634R        STA INPT2
4918  01612 047004         CMB,INB
4919  01613 040001         ADA 1
4920  01614 002126         CLE,SSA
4921  01615 043004         CMA,INA
4922  01616 042745R        ADA TEMP1
4923  01617 072745R        STA TEMP1
4924  01620 042616R        ADA DTMP5
4925  01621 072616R        STA DTMP5
4926  01622 002040         SEZ
4927  01623 036617R        ISZ DTMP5+1
4928*
4929  01624 062641R        LDA ABSTH
4930  01625 146260         MPY TEMP1
      01626 002745R
4931  01627 004040         CLE
4932  01630 042620R        ALA DTMP6
4933  01631 002040         SEZ
4934  01632 006004         INB
4935  01633 046621R        ALB DTMP6+1
4936  01634 136420         ISI DTMP6
      01635 002621R
4937  01636 036641R        ISZ ABSTH
4938  01637 066641R        LDB ABSTH
4939  01640 056046R        CPB =26
4940  01641 002001         RSS
4941  01642 027573R        JMP WDLP
4942  01643 146260         DLD DTMP5
      01644 002616R
4943  01645 161024         ASR 4
4944  01646 072765R        STA TEMP1
4945  01647 146260         DLD DTMP6
      01650 002620R
4946  01651 146460         DIV TEMP1
      01652 002745R
4947  01653 040404R        ADA =0=8
4948  01654 043404R        ADA =0=44
4949  01655 072606R        STA WIDTH
4950  01656 152001         OTA 1
4951  01657 127556R        JMP WFMSB,I
4952*
4953* MOMENT OF INERTIA OF ABS VAL OF DERIVITIVES OF QRS ABOUT FIDUCIAL POINT =
4954*
```

```
3958*   SIGMA[V*(ABS DV(N) + ABS DV(-N))] / SIGMA[ABS DV(N) + ABS DV(-N)]
3956*
3957*   AIOTM = 4*MOMENT OF INERTIA
3958*
3959    01600 164606V  WIDSH NOP
3960    01601 002406   CLA
3961    01602 072016R  STA OTMP5
3962    01603 072017R  STA OTMP5+1
3963    01604 072020R  STA OTMP6
3964    01605 072021R  STA OTMP6+1
3965    01606 166605P  LDB FPINX
3966    01607 147406R  AOB =D-15
3967    01670 076604R  STA INTEN
3968    01671 1.5028   GET RFCNT RATE ERROR
        01672 005015R
        01673 042245R
        01674 022250R
3969*
3970    01675 072033R  STA INPT1
3971    01676 072034R  STA INPT2
3972    01677 006404   CLR,INB
3973    01700 072041R  STB AOSTM
3974    01701 036024R  NULUP ADB INTEN
3975    01702 1.5028   GET RFCNT RATE ERROR
        01703 005015R
        01704 042245R
        01705 022250R
3976*
3977    01706 166033R  LDB INPT1
3978    01707 072033R  STA INPT1
3979    01710 007304   CRB,INB
3980    01711 140001   ALA 1
3981    01712 002128   SSA
3982    01713 003104   CMA,INA
3983    01714 072745R  STA TEMP1
3984*
3985    01715 006041R  LDB AOSTM
3986    01716 007304   CRB,INB
3987    01717 016004R  AOB INTEN
3988    01720 1.5028   GET RFCNT RATE ERROR
        01721 005015R
        01722 042245R
        01723 022250R
3989*
3990    01724 166034R  LDB INPT2
3991    01725 072034R  STA INPT2
3992    01726 007304   CRB,INB
3993    01727 140001   ALA 1
3994    01730 002128   CLE,SSA
3995    01731 003104   CMA,INA
3996    01732 042745R  ADA TEMP1
3997    01733 072745R  STA TEMP1
3998    01734 042016R  ADA OTMP5
3999    01735 072016R  STA OTMP5
4000    01736 002040   SEZ
4001    01737 036017R  ISZ OTMP5+1
4002*
4003    01740 062041R  LDA AOSTM
4004    01741 1.5028   MPY TEMP1
        01742 042745R
4005    01743 002404   CLE
4006    01744 042020R  ADA OTMP6
4007    01745 002040   SEZ
4008    01746 016004   INB
4009    01747 146021R  AOB OTMP6+1
4010    01750 154406R  OST OTMP6
        01751 072020R
4011    01752 036041R  ISZ AOSTM
4012    01753 006041R  LDB AOSTM
4013    01754 050004R  CPB 026
4014    01755 002001   RSS
4015    01756 027701R  JMP NULUP
4016    01757 164201   OLD OTMP5
        01760 072016R
4017    01761 1.1024   ASR 4
```

```
1019   01702 072745R        STA TEMP1
1019   01703 1.4210         OLD DTMP6
       01704 06202aR
1020   01705 104060R        DIV TEMP1
       01706 0027450R
1021   01707 043404R        ADA #0-8
1022   01770 0720405R       STA WIDTH
1023   01771 102001         ITA 1
1024   01772 127060R        JMP *105R,I
1025*
1026*   SUBROUTINE TO CALCULATE NOISE
1027*
1028   01773 0000000R  NOISB  NOP 1029   01774 002400        CLA
1030   01775 072052R       STA NABS
1031   01776 072053R       STA NABS+1
1032   01777 072010R       STA DTMP2
1033   02000 072011R       STA DTMP2+1
1034   02001 072053R       STA NOISE
1035   02002 072557R       STA 6TOBT
1036   02003 000050R       LDB RTOR
1037   02004 005121        ORS,ARS
1038   02005 047407R       ADB #0-6M
1039   02006 003410R       LDA #05M
1040   02007 105007        CMP
1041   02010 127773R       JMP NOISB,I
1042   02011 003411R       LDA #02M
1043   02012 105007        CMP
1044   02013 007705        CMA,INB,RSS
1045   02014 047412R       LDB #0-20M
1046   02015 072746R       STA TEMP2
1047   02016 076054R       STB NSCNT
1048   02017 047413R       ALS #0-3M
1049   02020 046003R       ADB FPINX
1050   02021 105751        CMY
1051   02022 105020        GET FINDX MATE ERROR
       02023 004017R
       02024 002240R
       02025 002250R
1052   02026 072745R       STA TEMP1
1053   02027 105770  NSLUP  ISY
1054   02030 036000        NOP
1055   02031 105750        CYA
1056   02032 105020        GET FINDX RATE ERROR
       02033 004017R
       02034 002240R
       02035 002250R
1057   02036 006745R       LDB TEMP1
1058   02037 072745R       STA TEMP1
1059   02040 007004        CMB,INB
1060   02041 040001        ADA 1
1061   02042 002621        SSA,RSS
1062   02043 003004        CMA,INA
1063   02044 105030        SAD NABS
       02045 002052R
1064   02046 104400        OST NABS
       02047 002052R
1065   02050 002745R       LDA TEMP1
1066   02051 002420        SOA              KEEP ABS VAL
1067   02052 003004        CMA,INA
1068   02053 105030        SAD DTMP2
       02054 002010R
1069   02055 104400        OST DTMP2
       02056 002010R
1070   02057 006054R       ISZ NSCNT
1071   02060 026027R       JMP NSLUP
1072*
1073   02061 104200        OLD NABS
       02062 002052R
1074   02063 100024        ASL 4
1075   02064 105031        DAD DTMP2
       02065 002010R
1076   02066 104040        DIV TEMP2
       02067 002745R
1077   02070 102201        SOC
```

```
1076    12071 063362R           LDA =H77777
1077    12072 012020            SSA
1080    12073 007401            CLB,RSS
1081    12074 000400            CLA
1082    12075 110032            ASL 10
1083    12076 160400            DIV WHITE
        12077 063012R
1084    12100 102201            SOC
1085    12101 063462R           LDA =H77777
1086    12102 072053R           STA NOISE
1087    12103 104201R           DLD OTMP2    BASELINE STUFF
        12104 002201R
1088    12105 160400            DIV TEMP2
        12106 002740R
1089    12107 003000            CMA,INA
1090    12110 072557R           STA OTOBT    NORMALIZED
1091    12111 127773R           JMP NOISR,I
1092*
1093*   SUBROUTINE TO ORDER FAMILIES BY POPULATION
1094*
1095    12112 000000  SORT      NOP
1096    12113 072745R           STA TEMP1
1097    12114 170032            ADV T1234 TORDR
        12115 002154R
        12116 002162R
1098    12117 002401            CLA,RSS
1099    12120 062745R SORTL     LDA TEMP2
1100    12121 012004            INA
1101    12122 052745R           CPA TEMP1
1102    12123 002405            CLA,INA,RSS
1103    12124 026132R           JMP SORT1
1104    12125 007400            CLB
1105    12126 016745R           ADB TEMP1
1106    12127 076745R           STB TEMP1
1107    12130 137400R           CPP =01
1108    12131 126112R           JMP SORT,I
1109    12132 072746R SORT1     STA TEMP2
1110    12133 042151R           ALA OTORD
1111    12134 072747R           STA TEMP3
1112    12135 104240            DLD R,I
        12136 100000
1113    12137 101741            CAX
1114    12140 105751            COY
1115    12141 101742            LAX POP
        12142 065206R
1116    12143 105752            LAY PCP
        12144 015206R
1117    12145 105017            CMP
1118    12146 026120R           JMP SORTL
1119    12147 101754            CYA
1120    12150 105744            CAP
1121    12151 104400            DST TEMP3,I
        12152 102747R
1122    12153 026120R           JMP SORTL
1123    12154 000001  T1234 DEC 1,2,3,4,5
        12155 000002
        12156 000003
        12157 000004
        12160 000005
1124    12161 002161R OTORD DEF *
1125    12162 000000  TORDR RSS 5
1126*
1127*   CALLED FOR INITIALIZATION OR ERROR CORRECTION
1128*
1129    12167 000000  CLAF      NOP
1130    12170 027064R           LDA CLRPT
1131    12171 004400            CLB
1132    12172 174000            CLEAR STB R,I
1133    12173 025065R           ADA NPAT
1134    12174 052765R           CPA ENDPT
1135    12175 002001            RSS
1136    12176 026172R           JMP CLEAR
1137    12177 063315R           LDA PFCNT
1138    12200 072622R           STA INDX
1139    12201 072017R           STA FINDX
1140    12202 063362R           LDA =0512
```

```
1141    1223 173014R         STA  HFLEN
1142    12224 172215R        STA  FILEN
1143    12225 126167R        JMP  CLBF,I
1144*
1145*   OUTPUT GRAPHICS
1146*
1147    12226 000000  GRPIC  NOP
1148    12227 141741         CAX
1149    12210 003400         CCA
1150    12211 103624         OTA  GVG,C
1151    12212 102224  SFC    SFC  GVG
1152    12213 026225R        JMP  INMOG
1153    12214 002400         CLA
1154    12215 001002         ELA
1155    12216 102124         STF  GVG
1156    12217 106724         CLC  GVG
1157    12220 103024         OTA  GVG,C
1158    12221 101744         CXA
1159    12222 105021         GRP  STC
        12223 002037R
1160    12224 126240R        JMP  GRPIC,I
1161    12225 101744  INMOG  CXA
1162    12226 002040         SEZ
1163    12227 026235R        JMP  ERINT
1164    12230 105021         GRP  CLF
        12231 002035R
1165    12232 126240R        JMP  GRPIC,I
1166    12233 105021  ERINT  GRP  SFC
        12234 002212R
1167    12235 126240R        JMP  GRPIC,I
1168*
1169*   CMP AS SUBROUTINE
1170*
1171    12236 000000  CMPAB  NOP
1172    12237 007004         CPA,INA
1173    12240 044002         ADA  2
1174    12241 007025         CAA,SSA,INA,RSS
1175    12242 006236R        ISZ  CMPAB
1176    12243 044002         ADA  2
1177    12244 126236R        JMP  CMPAB,I
1178*
1179*   SUBROUTINE TO GET FILTERED DATA
1180*
1181    12245 012545R  WATE  DEF  ????
1182    12246 000002         NOP              GIVE INTERUPTS A CHANCE
1183    12247 126545R        JMP  ????,I
1184*
1185*
1186*
1187*   FIX UP AFTER BUFFER OVERRUN
1188*
1189    12250 000000  ERROR  NOP
1190    12251 002400         CLA
1191    12252 073012R        STA  MHITE
1192    12253 003400         CCA
1193    12254 072560R        STA  MPATH
1194    12255 066022R        LDB  INDX
1195    12256 126062         GET  FINDX WATE DEF??
        12257 004178R
        12260 062245R
        12261 002263R
1196    12262 026062X        JMP  NUPAC
1197    12263 000000  DEF??  NOP
1198    12264 062017R        LDA  FINDX
1199    12265 072022R        STA  INDX
1200    12266 026002X        JMP  NUPAC
1201*
1202*   SUBROUTINE TO CALCULATE MATCH
1203*
1204    12267 000000  MSNAP  NOP
1205    12270 072745R        STA  TEMP1
1206    12271 002400         CLA
1207    12272 072012R        STA  CTMP3
1208    12273 072013R        STA  CTMP3+1
1209    12274 072014R        STA  CTMP4
```

```
1210   02275  072615R        STA OTMP4+1
1211   02276  105755         LDY #075
       02277  074146
1212   02300  105754  HSNLP  CYA
1213   02301  047415R        AUA #0-26
1214   02302  040000R        ALO FPINX
1215   02303  105020         GET FINDX WATE ERROR
       02304  014617R
       02305  062245R
       02306  042250R
1216*
1217   02307  105752         LDY TEMP1,I
       02310  102745R
1218   02311  101741         CAX
1219   02312  003004         CMA,INA
1220   02313  103101         CLO
1221   02314  040001         AUA 1
1222   02315  002125         CLE,SSA
1223   02316  003004         CMA,INA
1224   02317  102201         SOC
1225   02320  003004         CMA,INA
1226   02321  042014R        AUA OTMP4
1227   02322  002041         SEZ
1228   02323  036013R        ISZ OTMP4+1
1229   02324  072014R        STA OTMP4
1230   02325  101744         CXA
1231   02326  002125         SSA
1232   02327  003004         CMA,INA
1233   02330  002125         CLE,SSB
1234   02331  007004         CMA,INB
1235   02332  040001         AUA 1
1236   02333  042012R        AUA OTMP3
1237   02334  002041         SEZ
1238   02335  036013R        ISZ OTMP3+1
1239   02336  072012R        STA OTMP3
1240   02337  105771         OSY
1241   02340  026300R        JMP HSNLP
1242   02341  104200         OLD OTMP3
       02342  042612R
1243   02343  101031         ASR 9
1244   02344  072745R        STA TEMP1
1245   02345  104200         OLD OTMP4
       02346  042614R
1246   02347  101410         DIV TEMP1
       02350  042745R
1247   02351  124267R        JMP PSNAP,I
1248*
1249** SUBROUTINE TO COMPARE SNAPSHOTS
1250*
1251   02352  000000R  MSNSN NOP
1252   02353  072745R        STA TEMP1
1253   02354  072746R        STA TEMP2
1254   02355  104000         CLA
1255   02356  072012R        STA OTMP3
1256   02357  072013R        STA OTMP3+1
1257   02360  072014R        STA OTMP4
1258   02361  072015R        STA OTMP4+1
1259   02362  105755         LDY #075
       02363  074146
1260   02364  101752  MSSLP  LAY TEMP2,I
       02365  102746R
1261*
1262   02366  105752         LDY TEMP1,I
       02367  102745R
1263   02370  101741         CAX
1264   02371  003004         CMA,INA
1265   02372  103101         CLO
1266   02373  040001         AUA 1
1267   02374  002125         CLE,SSA
1268   02375  003004         CMA,INA
1269   02376  102201         SOC
1270   02377  003004         CMA,INA
1271   02400  042614R        AUA OTMP4
1272   02401  002041         SEZ
1273   02402  036015R        ISZ OTMP4+1
```

```
1274  02403  072014R        STA  OTMP4
1275  02404  101744         CXA
1276  02405  042124         SSA
1277  02406  003024         CMA,INA
1278  02407  006124         CLM,SSR
1279  02410  007024         CMA,INR
1280  02411  040001         ADA  1
1281  02412  042012R        ADA  OTMP3
1282  02413  002040         SEZ
1283  02414  056013R        TSZ  OTMP3+1
1284  02415  072012R        STA  OTMP3
1285  02416  105771         OSY
1286  02417  026364R        JMP  MSSLP
1287  02420  104200         OLD  OTMP3
      02421  002012R
1288  02422  101031         ASR  9
1289  02423  072245R        STA  TEMP1
1290  02424  104200         OLD  OTMP4
      02425  002014R
1291  02426  100400         DIV  TEMP1
      02427  002245R
1292  02430  126352R        JMP  MSNSN,I
1293*
1294*       SUBROUTINE TO UPDATE A SNAPSHOT
1295*
1296  02431  000000  USNAP  NOP
1297  02432  072245R        STA  TEMP1       SNAP POINTER
1298  02433  105755         LDY  =D125
      02434  007410R
1299  02435  105754  USNLP  CYB
1300  02436  047115R        ALM  =D-26
1301  02437  060000R        ALM  FPINX
1302  02440  105020         GET FINDX  RATE ERROR
      02441  004017R
      02442  022240R
      02443  002250R
1303*
1304  02444  105752         LMY  TEMP1,I     B TO OLD
      02445  002245R
1305  02446  007064         CMR,INR          B TO - OLD
1306  02447  040001         ADA  1           A TO NEW - OLD
1307  02450  007004         CMR,INR          B TO OLD
1308  02451  001121         ARS,ARS
1309  02452  001104         ARS              A TO (NEW - OLD)/8
1310  02453  044000         ADR  B           B TO UPDATED DATUM
1311  02454  105756         SBY  TEMP1,I
      02455  002245R
1312  02456  105771         OSY
1313  02457  026435R        JMP  USNLP
1314  02460  126431R        JMP  USNAP,I
1315*
1316*       SUBROUTINE TO DISPLAY SNAPSHOT
1317*
1318  02461  000000  DSNAP  NOP
1319  02462  072245R        STA  TEMP1       SNAP POINTER
1320  02463  052754R        LDA  NDSPT
1321  02464  007417R        LDR  =D-75
1322  02465  002010         CLE
1323  02466  016200R        JSR  GPPIC
1324  02467  105755         LDY  =D75
      02470  007414R
1325  02471  101752  DSNLP  LAY  TEMP1,I
      02472  002245R
1326  02473  043026R        ADA  =B146000
1327  02474  013421R        AND  =B177400
1328  02475  105754         CYB
1329  02476  003001         INR  1
1330  02477  101756         SAY  NDSM1,I
      02500  002755R
1331  02501  105771         OSY
1332  02502  126471R        JMP  DSNLP
1333  02503  002040         CLE
1334  02504  052754R        LDA  NDSPT
1335  02505  007417R        LDR  =D-75
1336  02506  016200R        JSR  GRPIC
1337  02507  126461R        JMP  DSNAP,I
```

```
1038*
1039*    SUBROUTINE TO STORE A SNAPSHOT
1040*
1041    02510  000000  NSNAP  NOP
1042    02511  072450         STA  TEMP1        SNAP POINTER
1043    02512  105755         LDY  =0125
        02513  007415R
1044    02514  105764  NSNLP  CYP
1045    02515  007415R        ADS  =0-26
1046    02516  060000R        ADR  FPINX
1047    02517  103520         GET FINDX RATE ERROR
        02520  004017R
        02521  022450
        02522  022510R
1048*
1049    02523  101750         SAY  TEMP1,I
        02524  102740R
1050    02525  105771         USY
1051    02526  026314R        JMP  NSNLP
1052    02527  126510R        JMP  NSNAP,I
1053*
1054    02530  000010  PTPTM  DEC  8            SAMPLES BETWEEN PEAKS OF FILTER
1055    02531  002532R FLAGR  DEF  *+1
1056    02532  004017R        DEF  FINDX
1057    02533  003195R        DEF  PFCNT
1058    02534  000012         DEC  8
1059    02535  002771R        DEF  WNDOW
1060    02536  103124  CLF    CLF  GVG
1061    02537  103724  STC    STC  GVG,C
1062    02540  112522  A/DHL  HLT  A/D
1063    02541  112510  PPOHL  HLT  PPO
1064    02542  112424  GVGHL  HLT  GVG
1065    02543  002543R LNPKG  DEF  *
1066    02544  000000  VFINX  NOP
1067    02545  000000  ????   NOP
1068    02546  000000  OLMHT  NOP
1069    02547  001750  HRDEV  DEC  1000
1070    02550  000000  CHAN   NOP
1071    02551  177740  BM40   OCT  -40
1072    02552  000000  NABS   BSS  2
1073    02554  000000  NSCNT  NOP
1074    02555  176031  DN999  DEC  -999
1075    02556  023417  D9999  DEC  9999
1076    02557  000000  RIOBT  NOP
1077    02560  000000  DSCNT  NOP
1078    02561  000377  DSLEN  OCT  377
1079    02562  000007  B7     OCT  7
1080    02563  177771  DN7    DEC  -7
1081    02564  177770  DN8    DEC  -8
1082    02565  000001  NPAT   DEC  1
1083    02566  000777  BUFL   OCT  777
1084    02567  000000  PEAK   NOP
1085    02570  000740  D484   DEC  484
1086    02571  000046  D38    DEC  38
1087    02572  000000  OUTCT  NOP
1088    02573  000001  OUT40  OCT  1
1089    02574  000000  FSTH   NOP
1090    02575  100000  DIGCW  OCT  100000
1091    02576  000000  LSINP  NOP
1092    02577  000000  LSCLT  NOP
1093    02600  177406  SECTR  DEC  -250
1094    02601  177712  TWAIT  DEC  -50
1095    02602  000000  TSAVE  NOP
1096    02603  177777  D11    DEC  -1
1097    00010          PPO    EQU  10B
1098    00022          A/D    EQU  22B
1099    00024          GVG    EQU  24B
1100    02604  000000  INTEN  NOP
1101    02605  000000  FPIX   NOP
1102    02606  000000  NCNT5  NOP
1103    02607  000000  NCNT6  NOP
1104    02610  000000  OTMP2  BSS  2
1105    02612  000000  OTMP3  BSS  2
1106    02614  000000  OTMP4  BSS  2
1107    02616  000000  OTMP5  BSS  2
1108    02620  000000  OTMP6  BSS  2
```

```
1409   02622  000000   INDX   NOP
1410   02623  100000   HINIT  OCT 100000
1411   02624  177400   H1774  OCT 177400
1412   02625  001540   DCONT  DEF CONT
1413   02626  000000   SA     NOP
1414   02627  000000   SB     NOP
1415   02630  000000   SX     NOP
1416   02631  000000   SY     NOP
1417   02632  000000   SEO    NOP
1418   02633  000000   IVPT1  NOP
1419   02634  000000   IVPT2  NOP
1420   02635  010400   LINE1  OCT 10400
1421   02636  003400   LINE2  OCT 3400
1422   02637  000006   D6     DEC 6
1423   02640  000032   D26    DEC 26
1424   02641  000000   ABSTM  NOP
1425   02642  000000   SIGN   NOP
1426   02643  000015   NDLT   OCT 15
1427   02644  020040   BASE   ASC 1
1428   02644           VRPT   EQU *-1
1429   02645  000000   DELAY  NOP
1430   02646  000000   WIDTH  NOP
1431   02647  000000   HCNT   NOP
1432   02650  000000   RTOR   NOP
1433   02651  000000   MATCH  NOP
1434   02652  000000   VCNT   NOP
1435   02653  000000   NOISE  NOP
1436   02654  000000   VFMTC  NOP
1437   02655  000000   SCAMP  NOP
1438   02656  000000   PHASE  NOP
1439   02657  000000   RTDMN  NOP
1440   02660  000000   VFTG   NOP
1441   02661  000000   ERLY   NOP
1442   02662  000015   VRCNT  ABS *-DELAY
1443   02663  002636   MSPT3  DEF BGMSG-3
1444   02664  002666   MSPT1  DEF HGMSG
1445   02665  002716   MSPT2  DEF MDMSG
1446   02666           BGMSG  EQU *
1447   02666  000000          BSS 2
1448   02670  060504          ASC 1, D
1449   02671  000000          BSS 2
1450   02672  060527          ASC 1, W
1451   02674  000000          BSS 2
1452   02675  060502          ASC 1, B
1453   02677  000000          BSS 2
1454   02701  060522          ASC 1, R
1455   02702  000000          BSS 2
1456   02704  060515          ASC 1, M
1457   02705  000000          BSS 2
1458   02707  060526          ASC 1, V
1459   02710  000000          BSS 2
1460   02712  060516          ASC 1, N
1461   02713  000000          BSS 2
1462   02715  060506          ASC 1, F
1463   02716           MDMSG  EQU *
1464   02716  000000          BSS 2
1465   02720  060501          ASC 1, A
1466   02721  000000          BSS 2
1467   02723  060520          ASC 1, P
1468   02724  000000          BSS 2
1469   02725  060525          ASC 1, U
1470   02727  000000          BSS 2
1471   02731  060503          ASC 1, C
1472   02732  000000          BSS 2
1473   02733  060522          ASC 1, R
1474   02735           ENMSG  EQU *
1475   02735  000030   MSLN1  ABS MDMSG+MDMSG-BGMSG-BGMSG
1476   02736  000032   MSLN2  ABS ENMSG+ENMSG-MDMSG-MDMSG
1477   02737  000000   N2     NOP
1478   02740  000000   N3     NOP
1479   02741  002741   ON     DEF *
1480   02742  000000   BUCTR  NOP
1481   02743  000000   LJCSC  NOP
1482   02744  000012   D10    DEC 10
1483   02745  000000   TEMP1  NOP
1484   02746  000000   TEMP2  NOP
```

```
1485   02747 000000   TEMP3 NOP
1486*  LAST BEAT PATHOLOGY: -1=UNKNOWN, 0=NORMAL, 1=VPB, 2=FLB
1487   02750 000000   BPATH NOP
1488   02751 000020   B20   OCT 20
1489   02752 003016R  ADBUF DEF ADBF
1490   02753 005244R  DSPNT DEF DSBF
1491   02754 005044R  NDSPT DEF NDSBF
1492   02755 005043R  NDSM1 DEF NDSBF-1
1493   02756 000005   RPRLY DEC 5
1494   02756          SWPAD EQU *-1
1495   02757 005750R        DEF FAM1-1
1496   02760 006153R        DEF FAM2-1
1497   02761 006335R        DEF FAM3-1
1498   02762 006540R        DEF FAM4-1
1499   02763 006742R  NGTM1 DEF FAM5-1
1500   02764 002771R  CLRPT DEF WNDOW
1501   02765 005244R  FNDPT DEF DSBF
1502   02766 000004   BTCNT DEC 4
1503   02767 000004   BTOUT DEC 4
1504   02770 005044R  BTBUF DEF NTBF
1505   02771 000000   WNDOW BSS 17
1506   03012 000000   WRITE NOP
1507   03013 000000   FRFLG NOP
1508   03014 001000   BFLEN DEC 512
1509   03015 000000   BFCNT NOP
1510   03016 000000   ADBF  BSS 512
1511   03016 001000   FILEN DEC 512
1512   03017 000000   FINDX NOP
1513   03020 000000   FLBF  BSS 512
1514   03017          WRINT EQU *-1
1515   03020 000000         BSS 4
1516   03024 001750   BRTDN DEC 1000
1517   03024          PUP   EQU *-1
1518   03025 000000         BSS 5
1519   03031          PATH  EQU *-1
1520   03032 000000         BSS 5
1521   03036          AGE   EQU *-1
1522   03037 000000         BSS 4
1523   03043 000000   NAGE  NOP
1524   03044 000000   BTBF  BSS 128
1525   03244 000000   DSBF  BSS 256
1526   03644 000000   NDSBF BSS 75
1527   03757 000000   FAM1  BSS 125
1528   04154 000000   FAM2  BSS 125
1529   04351 000000   FAM3  BSS 125
1530   04546 000000   FAM4  BSS 125
1531   04743 000000   FAM5  BSS 125
1532   07140 002000   PUNCT OCT 2000        SPACE/!"#$&'()*+,-./
       07341 177363
       07342 000777
       07345 176036
       07347 001750
       07350 001000
       07351 000220
       07352 177777
       07353 000002
       07354 001139
       07355 000070
       07356 177777
       07357 000077
       07370 000026
       07371 001000
       07372 000400
       07373 177740
       07374 177010
       07375 000036
       07376 100000
       07377 000000
       07400 000001
       07401 175430
       07402 175044
       07403 000002
       07404 177770
       07405 177724
       07406 177761
       07407 177774
```

What is claimed is:

1. In a patient monitoring system having an input to which signals derived from an ECG machine that represent the heartbeat cycle of a patient may be applied, the combination of means coupled to said input for giving information as to the location of a fiducial point in the signal representing each heartbeat cycle, said fiducial point being located at the centroid, memory means for storing one of said signals and information as to the location of its fiducial point, means for matching unknown signals representing heartbeat cycles with the one said heartbeat cycle that has been stored in such manner that their respective fiducial points are in time coincidence so as to provide at its output information as to the degree of correlation between each received signal and the said signal stored in said memory means, and means coupled to the output of said matching means for producing one indication when the unknown signal is ectopic and another indication when it is not ectopic.

2. The combination of an input to which ECG waves representing the heartbeat cycle of a patient may be applied, a QRS detector coupled to said input for giving information at its output as to the occurrence of a preliminary fiducial point of the ECG wave for each heartbeat cycle, fiducial point location means coupled to said input and to the output of said QRS detector for providing information as to the time of occurrence within each heartbeat cycle of a corrected fiducial point with respect to the time of occurrence of the preliminary fiducial point in accordance with the expression $$T = \frac{\int_{t_1}^{t_2} t \left(\frac{d^M V}{dt^M}\right)^n}{\int_{t_1}^{t_2} \left(\frac{d^M V}{dt^M}\right)^n}$$

memory means coupled to said input and to said fiducial point location means for storing an ECG waveform and information as to the time within that waveform at which its corrected fiducial point occurs, matching means coupled to said input and to said memory means for producing at its output signals indicative of the difference in form of the ECG waveform at said input with the waveform stored in said memory means in such manner that their corrected fiducial points are effectively in time coincidence, and means responsive to the signals including those produced by said matching means for indicating whether the ECG waveform derived from said input is ectopic.

3. The combination of an input to which ECG signals representing heartbeat cycles of a patient may be applied, fiducial point determining means coupled to said input for giving information as to the time of occurrence of the centroid of each heartbeat cycle, storage means coupled to the output of said fiducial point determining means for retaining information as to the time of occurrence of the centroid of the ECG wave representing one heartbeat cycle at least until information as to the time of occurrence of the centroid of the ECG wave representing the next heartbeat cycle is available, and means coupled to said storage means and said fiducial point determining means for providing a signal corresponding to the difference in time between the occurrence of the centroid of the ECG wave representing the said one heartbeat cycle and the time at which the centroid for a successive heartbeat cycle occurs.

4. The combination of an input to which ECG waves representing the heartbeat cycle of a patient may be applied, a QRS detector coupled to said input for giving information at its output as to the occurrence of a preliminary fiducial point of the ECG wave for each heartbeat cycle, fiducial point location means coupled to said input and to the output of said QRS detector for providing information as to the time of occurrence within each heartbeat cycle of a corrected fiducial point with respect to the time of occurrence of the preliminary fiducial point in accordance with the expression $$T = \frac{\int_{t_1}^{t_2} t \left(\frac{d^M V}{dt^M}\right)^n}{\int_{t_1}^{t_2} \left(\frac{d^M V}{dt^M}\right)^n},$$

storage means coupled to the output of said fiducial point determining means for retaining information as to the time of occurrence of the centroid of the ECG wave representing one heartbeat cycle at least until information as to the time of occurrence of the centroid of the ECG wave representing the next heartbeat cycle is available, and means coupled to said storage means and said fiducial point determining means for providing a signal corresponding to the difference in time between the occurrence of the centroid of the ECG wave representing the said one heartbeat cycle and the time at which the centroid for a successive heartbeat cycle occurs.

5. Apparatus for determining the difference in time between the time of a fiducial point of an ECG wave and a reference time comprising in combination, an input to which a signal representing an ECG wave may be applied, means for providing an indication representing a reference time, means for deriving a first signal representing the variation of one of a group of derivatives including the zero order derivative, with respect to time of an ECG wave applied to said input, means for providing a second signal representing the first signal raised to a power, means for providing a third signal representing the time elapsed from the reference time, means for deriving a fourth signal representing the product of the values represented by said second and third signals respectively, means for producing a fifth signal representing the effective integration of the values represented by said fourth signal between times which define a period including at least a portion of the ECG waveform, means for producing a sixth signal representing the effective integration of the values represented by said second signal over said period, and means for deriving a seventh signal representing the division of the value represented by said fifth signal by the value represented by said sixth signal, the seventh signal representing the difference in time between the reference time and the fiducial point for the ECG wave.

* * * * *